(12) United States Patent
Yen

(10) Patent No.: US 12,161,697 B2
(45) Date of Patent: *Dec. 10, 2024

(54) NANOSPHERES FOR BONE FRACTURE

(71) Applicant: Richard C. K. Yen, Yorba Linda, CA (US)

(72) Inventor: Richard C. K. Yen, Yorba Linda, CA (US)

( * ) Notice: Subject to any disclaimer, the term of this patent is extended or adjusted under 35 U.S.C. 154(b) by 937 days.

This patent is subject to a terminal disclaimer.

(21) Appl. No.: 17/094,114

(22) Filed: Nov. 10, 2020

(65) Prior Publication Data

US 2021/0060134 A1    Mar. 4, 2021

Related U.S. Application Data

(60) Continuation-in-part of application No. 15/233,779, filed on Aug. 10, 2016, now Pat. No. 11,260,109, which is a continuation-in-part of application No. 13/560,727, filed on Jul. 27, 2012, now abandoned, and a continuation-in-part of application No. 14/226,544, filed on Mar. 26, 2014, now Pat. No. 9,629,931, which is a continuation-in-part of application No. 12/927,543, filed on Nov. 16, 2010, now Pat. No. 9,226,898, and a continuation-in-part of application No. 13/560,727, filed on Jul. 27, 2012, now abandoned, and a continuation-in-part of application No. 13/604,770, filed on Sep. 6, 2012, now Pat. No. 9,351,925, and a continuation-in-part of application No. 13/605,765, filed on Sep. 6, 2012, now Pat. No. 9,504,641, said application No. 15/233,779 is a continuation-in-part of application No. 14/925,506, filed on Oct. 28, 2015, now abandoned, which is a continuation-in-part of application No. 13/560,727, filed on Jul. 27, 2012, now abandoned, and a continuation-in-part of application No. 13/604,770, filed on Sep. 6, 2012, now Pat. No. 9,351,925, said application No. 14/925,506 is a continuation-in-part of application No. 13/650,765, filed on Sep. 6, 2012, now Pat. No. 9,504,641, application No. 17/094,114, filed on Nov. 10, 2020 is a continuation-in-part of application No. 14/953,066, filed on Nov. 27, 2015, now abandoned, which is a division of application No. 12/927,543, filed on Nov. 16, 2010, now Pat. No. 9,226,898, application No. 17/094,114, filed on Nov. 10, 2020 is a continuation-in-part of application No. 16/505,257, filed on Jul. 8, 2019, now Pat. No. 11,260,110, which is a continuation-in-part of application No. 15/233,779, filed on Aug. 10, 2016, now Pat. No. 11,260,109, and a continuation-in-part of application No. 15/618,234, filed on Jun. 9, 2017, now Pat. No. 10,603,287, said application No. 16/505,257 is a continuation-in-part of application No. 15/238,928, filed on Aug. 17, 2016, now abandoned.

(60) Provisional application No. 61/853,041, filed on Mar. 27, 2013, provisional application No. 61/573,630, filed on Sep. 10, 2011, provisional application No. 61/627,623, filed on Oct. 14, 2011, provisional application No. 61/573,630, filed on Sep. 10, 2011, provisional application No. 61/627,623, filed on Oct.

(Continued)

(51) Int. Cl.
| | |
|---|---|
| *A61K 38/38* | (2006.01) |
| *A61K 9/00* | (2006.01) |
| *A61K 9/16* | (2006.01) |
| *A61K 9/51* | (2006.01) |

(52) U.S. Cl.
CPC .......... *A61K 38/385* (2013.01); *A61K 9/0019* (2013.01); *A61K 9/16* (2013.01); *A61K 9/5169* (2013.01); *A61K 38/38* (2013.01)

(58) Field of Classification Search
None
See application file for complete search history.

(56) References Cited

U.S. PATENT DOCUMENTS

| | | | |
|---|---|---|---|
| 4,440,679 A | 4/1984 | Fernandes et al. | |
| 5,679,377 A | 10/1997 | Bernstein et al. | |

(Continued)

FOREIGN PATENT DOCUMENTS

| | | |
|---|---|---|
| CN | 103566360 A | 2/2014 |
| CN | 103841989 A | 6/2014 |

(Continued)

OTHER PUBLICATIONS

Everts, P.A.M., et al. 2006 JECT 38: 174-187. (Year: 2006).*

(Continued)

*Primary Examiner* — Marsha Tsay
(74) *Attorney, Agent, or Firm* — David Guerra

(57) ABSTRACT

A product and method of using albumin nanoparticles for stimulating bone heal by augmenting the function or effectiveness of stem cells or precursor cells in vivo. An albumin nanoparticle suspension containing submicron albumin spheres is prepared, with the albumin spheres being capable of augmenting a function and effectiveness of stem cells or precursor cells in vivo for healing bone fractures. A predetermined amount of the albumin nanoparticle suspension is administered to a patient after an onset of a bone fracture or bone injury. A function of the stem cells or precursor cells are augmented or improved by the albumin spheres to repair cellular or tissue damage associated with a fracture bone, resulting in decreasing mortality or morbidity of the patient. The albumin spheres can be bound with fibrinogen molecules in vitro or in vivo.

11 Claims, 5 Drawing Sheets

Related U.S. Application Data 14, 2011, provisional application No. 61/281,466, filed on Nov. 18, 2009, provisional application No. 62/230,629, filed on Jun. 11, 2015, provisional application No. 62/733,468, filed on Sep. 19, 2018, provisional application No. 62/364,764, filed on Jul. 20, 2016.

(56) References Cited

U.S. PATENT DOCUMENTS

| | | |
|---|---|---|
| 6,221,668 B1 | 4/2001 | Ryan et al. |
| 6,262,019 B1 | 7/2001 | Keller et al. |
| 6,264,988 B1 | 7/2001 | Yen |
| 6,916,795 B1 | 7/2005 | Youssef |
| 7,625,878 B2 | 12/2009 | Stella et al. |
| 9,114,127 B2 | 8/2015 | Yen |
| 9,226,898 B1 | 1/2016 | Yen |
| 9,351,925 B2 | 5/2016 | Yen |
| 9,504,641 B2 | 11/2016 | Yen |
| 9,629,931 B2 | 4/2017 | Yen |
| 10,603,287 B2 | 3/2020 | Yen |
| 2002/0004522 A1 | 1/2002 | Mueller et al. |
| 2002/0142046 A1 | 10/2002 | Yen |
| 2004/0043077 A1 | 3/2004 | Brown |
| 2004/0071715 A1 | 4/2004 | Schwendeman et al. |
| 2009/0304804 A1 | 12/2009 | Yen |
| 2009/0306186 A1 | 12/2009 | Jackson et al. |
| 2011/0189299 A1 | 8/2011 | Okubo et al. |
| 2011/0225661 A1 | 9/2011 | Deng et al. |
| 2011/0251127 A1 | 10/2011 | Yen |
| 2013/0064864 A1 | 3/2013 | Yen |
| 2013/0064865 A1 | 3/2013 | Yen |
| 2014/0030347 A1 | 1/2014 | Yen |
| 2014/0212358 A1 | 7/2014 | Yen |
| 2016/0045573 A1 | 2/2016 | Yen |
| 2016/0082086 A1 | 3/2016 | Yen |
| 2016/0354481 A1 | 12/2016 | Yen |
| 2016/0375105 A1 | 12/2016 | Yen |
| 2017/0128545 A9 | 5/2017 | Yen |
| 2018/0021264 A1 | 1/2018 | Yen |
| 2019/0328844 A1 | 10/2019 | Yen |

FOREIGN PATENT DOCUMENTS

| | | |
|---|---|---|
| CN | 109010804 A | 12/2018 |
| EP | 2753394 A1 | 7/2014 |
| WO | 2013036902 A1 | 3/2013 |
| WO | 2014018066 A2 | 1/2014 |

OTHER PUBLICATIONS

White, A. A., Panjabi, M. M., & Southwick, W. O. (1977). The four biomechanical stages of fracture repair. The Journal of Bone and Joint Surgery. American vol. 59(2), 188192.

Borsalino, G., Bagnacani, M., Bettati, E., Fornaciari, F., Rocchi, R., Uluhogian, S., Traina, G. C. (1988). Electrical stimulation of human femoral intertrochanteric osteotomies. Double-blind study. Clinical Orthopaedics and Related Research, (237), 256263.

Sharrard, W. J. (1990). A double-blind trial of pulsed electromagnetic fields for delayed union of tibial fractures. The Journal of Bone and Joint Surgery. British vol. 72(3), 347355.

Mammi GI1, Rocchi R, Cadossi R, Massari L, T. G. (1993). The electrical stimulation of tibial osteotomies. Double-blind study.—PubMed—NCBI. Clin Orthop Relat Res.

Yen, 1995, "A Novel Approach to Correcting the Bleeding Associated with Thrombocytopenia", Presented to American Association of Blood Banks: 48th annual meeting, Nov. 11-15, 1995.

Blajchman, 1996, "Evaluation of the in vivo Hemostatic Function of Human Platelets and Platelet Substitutes in a Thrombocytopeniabbit Model", In "Frozen Platelets and Platelet Substitutes in Transfusion Medicine" Mar. 7, 1996.

Muller et al, Pharmaceutical Research, vol. 13, No. 1, 32-37 (Year: 1996).

Shope et al., "Radiation-induced Skin Injuries from Fluoroscopy", RadioGraphy 1996, 16:1195-1199.

Asahara, T., Murohara, T., Sullivan, A., Silver, M., van der Zee, R., Li, T., Isner, J. M. (1997). Isolation of Putative Progenitor Endothelial Cells for Angiogenesis. Science, 275(5302), 964966.

Yang, 1998, "Distinct Cellular Interactions of Secreted and Transmembrane Ebola Virus Glycoproteins", Science Feb. 13, 1998:279 (5353):1034-7.

Kawaguchi, H., Nakamura, K., Tabata, Y., Ikada, Y., Aoyama, I., Anzai, J., Tamura, M. (2001). Acceleration of fracture healing in nonhuman primates by fibroblast growth factor-2. The Journal of Clinical Endocrinology and Metabolism, 86(2), 875880.

Smiley et al., "Fibrinogen stimulates macrophate chemokine secretion through toll-like receptor 4" J Immunol. Sep. 1, 2001; 167(5) abstract.

Hosseini et al., "Study of the Heat-Treated Human Albumin Stabilization by Caprylate and Acetyltryptophanate", Dept. of R&D, Blood Research and Fractionation Co., Tehran, Iran, Iranian Biomedical Journal 6 (4): /35-140 (Oct. 2002.

Rendell, M. S. et al. Skin blood flow response in the rat model of wound healing: Expression of vasoactive factors. J. Surg. Res. 107, 1826 (2002).

Sullican, 2003, "Ebola Virus Pathogenesis: Implications for Vaccines and Therapies", doi: 10.1128/JVI.77.18.9733-9737.2003, J. Virol. Sep. 2003 vol. 77 No. 18 9733-9737.

Woolf, A. D., & Akesson, K. (2003). Preventing fractures in elderly people. BMJ (Clinical Research Ed.), 327(7406), 8995.

Empana, J.-P., Dargent-Molina, P., Brart, G., & EPIDOS Group. (2004). Effect of Hip Fracture on Mortality in Elderly Women: The EPIDOS Prospective Study. Journal of the American Geriatrics Society, 52(5), 685690.

Sanchez, 2004, "Analysis of Human Peripheral Blood Samples from Fatal and Nonfatal Cases of Ebola (Sudan) Hemorrhagic Fever: Cellular Responses, Virus Load, and Nitric Oxide Levels", J. Virol. Oct. 2004 vol. 78No. 19 10370-10377.

World Health Organization, "Guidelines on viral inactivation and removal procedures intended to assure the viral safety of human blood plasma products", Annex 4, WHO Technical Report, Series No. 924, 2004.

Corbel, C., Vaigot, P., & Salan, J. (2005). (alpha)IIb Integrin, a novel marker for hemopoietic progenitor cells. The International Journal of Developmental Biology, 49(23), 279284.

Gaugler, 2005, "A Unifying System: Does the Vascular Endothelium Have a Role to Play in Multi-organ Failure Following Radiation Exposure?", BJR Suppl. 2005;27:100-5.

Lu, C., Miclau, T., Hu, D., Hansen, E., Tsui, K., Puttlitz, C., & Marcucio, R. S. (2005). Cellular basis for age-related changes in fracture repair. Journal of Orthopaedic Research, 23(6), 13001307.

Reiter et al., "Vitamin E and excessive bleeding" Ugeskr Laeger, Dec. 5, 2005; 167(49) (abstract.

Bottle, A., & Aylin, P. (2006). Mortality associated with delay in operation after hip fracture: observational study. BMJ (Clinical Research Ed.), 332(7547), 947951.

Coln-Emeric, C. S., & Saag, K. G. (2006). Osteoporotic fractures in older adults. Best Practice & Research. Clinical Rheumatology, 20(4), 695706.

Franceschi, C., Bonaf, M., Valensin, S., Olivieri, F., De Luca, M., Ottaviani, E., & De Benedictis, G. (2006). Inflamm-aging: An Evolutionary Perspective on Immunosenescence. Annals of the New York Academy of Sciences, 908(1), 244254.

Li, 2006, "The Preclinical and Clinical Trial of Platelet Substitute—Fibrinoplate" , 4th Asian Pacific Congress on Thrombosis and Haemostasis, Suzhou, China, Sep. 23, 2006.

Manjunatha, Antiboagulant proteins from snake venoms:structure, function and mechanism. Biochem J. (2006) 397, 377-387.

Hutchinson, 2007, "Cytokine and Chemokine Expression in Humans Infected with Sudan Ebola Virus", Reprints or correspondence: Dr. Karen L. Hutchinson, Special Pathogens Branch, MS G-14, Centers for Disease Control and Prevention, 1600 Clifton Rd. NE, Atlanta, GA 30333 (kbh6@cdc.gov.

(56) References Cited

OTHER PUBLICATIONS

Kakar, S., Einhorn, T. A., Vora, S., Miara, L. J., Hon, G., Wigner, N. A., Barnes, G. L. (2007). Enhanced chondrogenesis and Wnt signaling in PTH-treated fractures. Journal of Bone and Mineral Research: The Official Journal of the American Society for Bone and Mineral Research, 22(12), 19031912.

Pietri, M., & Lucarini, S. (2007). The orthopaedic treatment of fragility fractures. Clinical Cases in Mineral and Bone Metabolism: The Official Journal of the Italian Society of Osteoporosis, Mineral Metabolism, and Skeletal Diseases, 4(2), 108116.

Lee, D. Y., Cho, T.-J., Kim, J. A., Lee, H. R., Yoo, W. J., Chung, C. Y., & Choi, I. H. (2008). Mobilization of endothelial progenitor cells in fracture healing and distraction osteogenesis. Bone, 42(5), 932941.

Lelovas, P. P., Xanthos, T. T., Thoma, S. E., Lyritis, G. P., & Dontas, I. A. (2008). The laboratory rat as an animal model for osteoporosis research. Comparative Medicine, 58(5), 424430.

Mollon, B., da Silva, V., Busse, J. W., Einhorn, T. A., & Bhandari, M. (2008). Electrical Stimulation for Long-Bone Fracture-Healing: A Meta-Analysis of Randomized Controlled Trials. The Journal of Bone and Joint Surgery-American vol. 90(11), 23222330.

Paksima, N., Koval, K. J., Aharanoff, G., Walsh, M., Kubiak, E. N., Zuckerman, J. D., & Egol, K. A. (2008). Predictors of mortality after hip fracture: a 10-year prospective study. Bulletin of the NYU Hospital for Joint Diseases, 66(2), 111117.

Kutler et al., Annu Rev Med; 2009, 60:193-206.

Kuzyk, P. R., & Schemitsch, E. H. (2009). The science of electrical stimulation therapy for fracture healing. Indian Journal of Orthopaedics, 43(2), 127131.

Mundi, R., Petis, S., Kaloty, R., Shetty, V., & Bhandari, M. (2009). Low-intensity pulsed ultrasound: Fracture healing. Indian Journal of Orthopaedics, 43(2), 132140.

Tilling, L., Chowienczyk, P., & Clapp, B. (2009). Progenitors in motion: mechanisms of mobilization of endothelial progenitor cells. British Journal of Clinical Pharmacology, 68(4), 484492.

Victoria, G., Petrisor, B., Drew, B., & Dick, D. (2009). Bone stimulation for fracture healing: What's all the fuss? Indian Journal of Orthopaedics, 43(2), 117120.

Adachi JD, Adami S, Gehlbach S, et al. Impact of prevalent fractures on quality of life: Baseline results from the global longitudinal study of osteoporosis in women. Mayo Clin Proc 2010;85:806-813.

Becker DJ, Yun H, Kilgore ML, et al. Health services utilization after fractures: evidence from Medicare. J Gerontol A Biol Sci Med Sci 2010; 65:1012-1020.

K. Atesok, R. Li, D. J. Stewart, and E. H. Schemitsch, "Endothelial progenitor cells promote fracture healing in a segmental bone defect model," Journal of Orthopaedic Research, vol. 28, No. 8, p. 10071014, 2010.

N. E. Fedorovich, R. T. Haverslag, W. J. Dhert, and J. Alblas, "The role of endothelial progenitor cells in prevascularized bone tissue engineering: development of heterogeneous constructs," TissPart A, vol. 16, No. 7, pp. 23552367, 2010.

Carragee, E. J., Hurwitz, E. L., & Weiner, B. K. (2011). A critical review of recombinant human bone morphogenetic protein-2 trials in spinal surgery: emerging safety concerns and lessons learned. The Spine Journal: Official Journal of the North American Spine Society, 11(6), 471491.

Perdomo et al., "Quinine-induced thrombocytopenia: drug-dependent GPIb/IX antibodies inhibit megakaryocyte and proplatelet production in vitro". Blood Jun. 2, 2011 vol. 117 No. 225975-5986.

R. Li, K. Atesok, A. Nauth et al., "Endothelial progenitor cells for fracture healing: a microcomputed tomography and biomechanical analysis," Journal of Orthopaedic Trauma, vol. 25, No. 8, p. 467471, 2011.

Young, Y., Xiong, K., & Pruzek, R. M. (2011). Longitudinal Functional Recovery After Postacute Rehabilitation in Older Hip Fracture Patients: The Role of Cognitive Impairment and Implications for Long-Term Care. Journal of the American Medical Directors Association, 12(6), 431438.

Atesok, K., Matsumoto, T., Karlsson, J., Asahara, T., Atala, A., Doral, M. N., Schemitsch, E. (2012). An emerging cell-based strategy in orthopaedics: endothelial progenitor cells. Knee Surgery, Sports Traumatology, Arthroscopy, 20(7), 13661377.

C. Seebach, D. Henrich, K. Wilhelm, J. H. Barker, and I. Marzi, "Endothelial progenitor cells improve directly and indirectly early vascularization of mesenchymal stem cell-driven bone regeneration in a critical bone defect in rats," Cell Transplantation, vol. 21, No. 8, pp. 16671677, 2012.

Dent-Acosta, R. E., Storm, N., Steiner, R. S., & San Martin, J. (2012). The tactics of modern-day regulatory trials. The Journal of Bone and Joint Surgery. American vol. 94 Suppl 1(Suppl 1), 3944.

Elzoghby et al, Journal of Controlled Release, 157, 168-182 (Year: 2012).

Elzoghby et al, Journal of Controlled Release, 2012, 157, 168-182 (Year: 2012).

Nauth et al., "Stem Cells for the Repair and Regeneration of Bone" published in Indian J Orthop. Jan.-Feb. 2012; 46(1): 19-21.

Rithidech, 2012, "Attenuation of Oxidative Damage and Inflammatory Responses by Apigenin Given to Mice After Irradiation", Mutat Res. Dec. 12, 2012;749(1-2):29-38. doi: 10.1016/j.mrgentox.2012.08.001. Epub Aug. 15, 2012.

CDC, 2013, "Acute Radiation Syndrome Fact Sheet for Physicians", http://www.bt.cdc.gov/radiation/arsphysicianfactsheet.asp, Page last reviewed: Oct. 22, 2013, Page last updated: Aug. 21, 2014.

Winslow, 2013, "Oxygen: the Poison is in the Dose, Transfusion", Feb. 2013;53(2):424-37, doi: 10.1111/.1537-2995.2012.03774.x. Epub Jul. 15, 2012.

CDC, 2014, "Questions and Answers on Ebola", CDC: Page last reviewed: Oct. 24, 2014, Page last updated: Oct. 24, 2014.

CDC, 2014, "Signs and Symptoms of Ebola", CDC: Page last reviewed: Oct. 18, 2014, Page last updated: Oct. 18, 2014.

Chen, 2014, "Edaravone Protects Human Peripheral Blood Lymphocytes from Gamma Irradiation-induced Apoptosis and DNA Damage", Cell Stress Chaperones, Sep. 3, 2014.

Higgins, 2014, "Ebola Facts: How Many Ebola Cases are Outside of West Africa?", by Andrew Higgins Oct. 17, 2014, New York Times.

Kalamida, 2014, "Important Role of Autophagy in Endothelial Cell Response to Ionizing Radiation", PLoS One 9(7):e102408. doi:10.1371/journal.pone.0102408.

Kelland, 2014, "More Cases of Ebola in Europe 'Unavoidable', WHO says", Reuters.com, Kate's Feed EMEA Health and Science Correspondent, Oct. 8, 2014.

King, 2014, "Ebola Virus Infection", http://emedicine.medscape.com/article/216288-overview.

Peplow, P. V. (2014). Growth factor- and cytokine-stimulated endothelial progenitor cells in post-ischemic cerebral neovascularization. Neural Regeneration Research, 9(15), 14251429.

Sung, 2014, "Fibrinogen Coasted Nanospheres Prevent Thrombocytopenia-related Bleeding", American Society of Hematologists annual meeting, Dec. 2014.

European Commission, "Commission Implementing Decision (Dec. 2, 2015)", EU orphan designation No. EU/3/15/1442, Feb. 12, 2015.

European Medicines Agency, "Public summary of opinion on orphan designation", EMA/COMP/55779/2015, Committee for Orphan Medicinal Products, Mar. 30, 2015.

Morse, A., Yu, N. Y. C., Peacock, L., Mikulec, K., Kramer, I., Kneissel, M., Little, D. G. (2015). Endochondral fracture healing with external fixation in the Sost knockout mouse results in earlier fibrocartilage callus removal and increased bone volume fraction and strength. Bone, 71, 155163.

Xiao We Mao et al., "Effects of Fibrinoplate-S in a Radiated Mice Model" , an abstract at the Radiation Research Society Annual Meeting held in Weston, FL, Sep. 19-22, 2015.

Yasukochi et al., "Radiation-induced skin ulcer and rib fractures following percutaneous coronary internetion (PCI): A case of right back skin ulcer and adjacent rib fracture after single PCI", J. Dermatol,Mar. 20, 2015, doi: 10.1111/1346-8138.12839.

Buza, J. A., Einhorn, T., & Einhorn, T. (2016). Bone healing in 2016. Clinical Cases in Mineral and Bone Metabolism: The Official Journal of the Italian Society of Osteoporosis, Mineral Metabolism, and Skeletal Diseases, 13(2), 101105.

(56) References Cited

OTHER PUBLICATIONS

Cecchi, S., Bennet, S. J., & Arora, M. (2016). Bone morphogenetic protein-7: Review of signalling and efficacy in fracture healing. Journal of Orthopaedic Translation, 4, 2834.

Kawakami, Y., Matsumoto, T., Mifune, Y., Fukui, T., Patel, K., Walker, G., Kuroda, R. (2016). Therapeutic Potential of Endothelial Progenitor Cells in the Field of Orthopaedics. Current Stem Cell Research & Therapy, 12(1), 313.

Bates, B. D., Godbout, C., Ramnaraign, D. J., Schemitsch, E. H., & Nauth, A. (2017). Delayed Endothelial Progenitor Cell Therapy Promotes Bone Defect Repair in a Clinically Relevant Rat Model. Stem Cells International, 2017, 110.

Clark, D., Nakamura, M., Miclau, T., & Marcucio, R. (2017). Effects of Aging on Fracture Healing. Current Osteoporosis Reports, 15(6), 601608.

Kostenuik, P., & Mirza, F. M. (2017). Fracture healing physiology and the quest for therapies for delayed healing and nonunion. Journal of Orthopaedic Research : Official Publication of the Orthopaedic Research Society, 35(2), 213223.

Rajfer RA, Kilic A, Neviaser AS, Schulte LM, Hlaing S, Landeros J, Ebramzadeh E, Ferrini MF, Park SY. Acceleration of Fracture Healing in the Rat Induced by Upregulators of Nitric Oxide Synthase. Bone & Joint Research. 2017, 6(2):90-97.

Schandelmaier, S., Kaushal, A., Lytvyn, L., Heels-Ansdell, D., Siemieniuk, R. A. C., Agoritsas, T., Busse, J. W. (2017). Low intensity pulsed ultrasound for bone healing: systematic review of randomized controlled trials. BMJ (Clinical Research Ed.), 356, j656.

Kuroyanagi G:, Adapala N.S., Yamaguchi R., Kamiya N., Deng Z., Aruwajoye O., Kutschke M, Chen E., Jo C., Ren Y, Kim H.K.W., Interleukin-6 deletion stimulates revascularization and new bone formation following ischemic osteonecrosis in a murine model, Bone, 2018.

Sanghani-Kerai, A., McCreary, D., Lancashire, H., Osagie, L., Coathup, M., & Blunn, G. (2018). Stem Cell Interventions for Bone Healing: Fractures and Osteoporosis. Current Stem Cell Research & Therapy, 13(5), 369377.

Wagner, D. R., Karnik, S., Gunderson, Z. J., Nielsen, J. J., Fennimore, A., Promer, H. J., Li, J. (2019). Dysfunctional stem and progenitor cells impair fracture healing with age. World Journal of Stem Cells, 11(6), 281296.

* cited by examiner

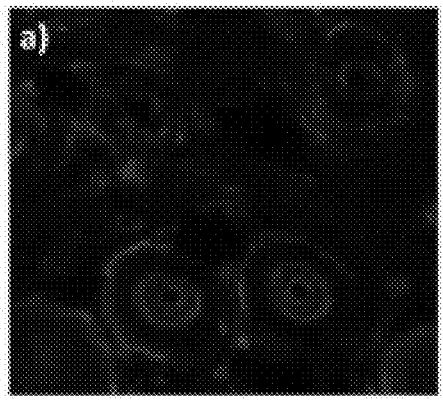
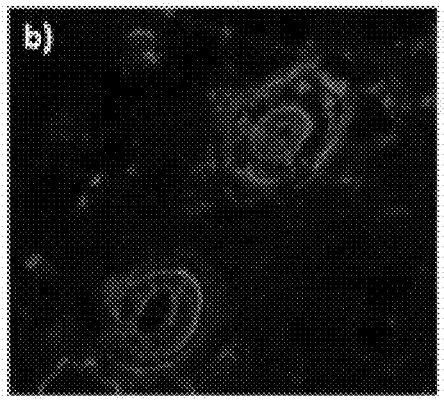
FIG. 3a         FIG. 3b
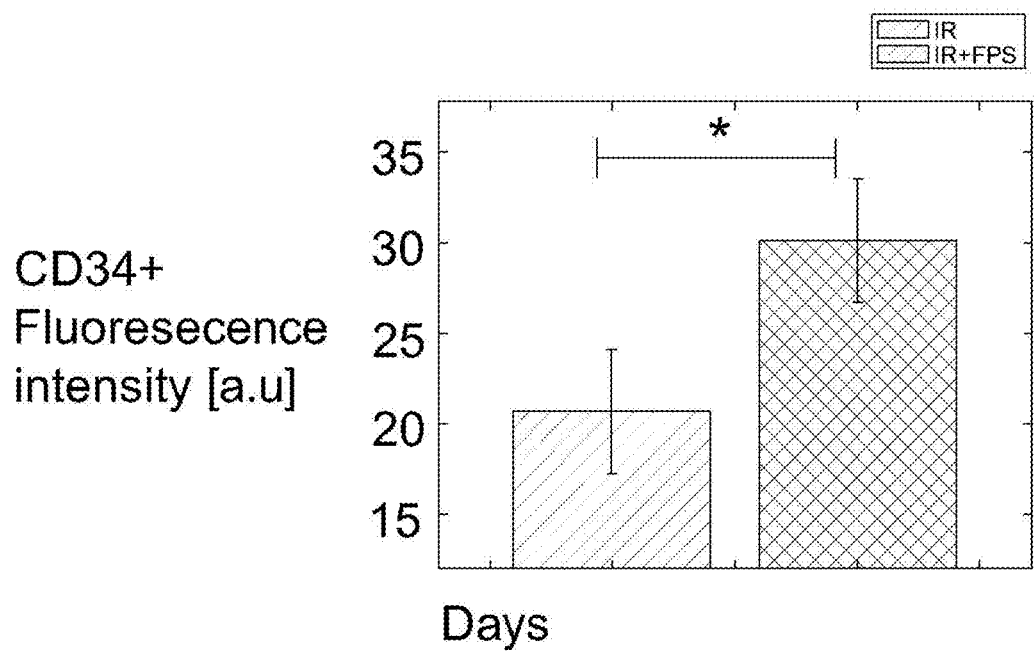
FIG. 4

NANOSPHERES FOR BONE FRACTURE

CROSS-REFERENCE TO RELATED APPLICATION

This application claims the benefit of priority of and is a Continuation-In-Part under 35 U.S.C. § 120 based upon co-pending U.S. patent application Ser. No. 16/505,257 filed on Jul. 8, 2019, which claims priority to U.S. provisional patent application No. 62/733,468 filed Sep. 19, 2018, and which is a Continuation-In-Part of U.S. patent application Ser. No. 15/233,779 filed on Aug. 10, 2016, U.S. patent application Ser. No. 15/618,234 filed on Jun. 9, 2017, U.S. patent application Ser. No. 15/238,928 filed on Aug. 17, 2016, and U.S. patent application Ser. No. 14/956,066 filed on Nov. 27, 2015.

This application claims the benefit of priority of and is a Continuation-In-Part under 35 U.S.C. § 120 based upon co-pending U.S. patent application Ser. No. 15/233,779 filed on Aug. 10, 2016, which claims priority to U.S. provisional patent application No. 62/230,629 filed Jun. 11, 2015, and which is a Continuation-In-Part of U.S. patent application Ser. No. 13/560,727 filed on Jul. 27, 2012, U.S. patent application Ser. No. 14/226,544 filed on Mar. 26, 2014, and U.S. patent application Ser. No. 14/925,506 filed on Oct. 28, 2015.

This application claims the benefit of priority of and is a Continuation-In-Part under 35 U.S.C. § 120 based upon co-pending U.S. patent application Ser. No. 14/953,066 filed on Nov. 27, 2015, which is a divisional application of U.S. application Ser. No. 12/927,543 filed on Nov. 16, 2010, which claims priority to U.S. provisional patent application No. 61/281,466 filed Nov. 18, 2009.

The entire disclosures of the prior provisional and non-provisional applications are incorporated herein by reference.

BACKGROUND

Technical Field

The present technology relates to nanospheres product, system and method for healing bone fractures for use in connection with promoting healing of fractured bones, in a surgical setting and non-surgical setting.

Background Description

Broken bones occur frequently in all populations, but more so in the elderly population whose bone density is less robust than in younger people. In certain populations e.g. the military, bones are not only broken by firearms shot by the enemy, but often by trucks or other heavy equipment falling on soldiers during training exercises in peaceful times.

The most common practice to promote healing is to bring the patient to a medical center where the fractured pieces are lined up by mechanical means and the patient is immobilized to some extent so that the broken ends can re-join each other during this healing period to form a bone-in-one-piece. Most such treatments are done by a surgical team. However, some broken bone can heal quite well spontaneous without surgery, e.g. the collar bone. In contrast, there are traumas where the bone is crushed or the bone is so severely damaged that there is no hope of the two ends ever re-joining to provide adequate mechanical function for the patient.

There are known systems or methods to bring about accelerated healing of fractured bones. One example is published in Bone Joint Research 2017; 6:90-97, titled "Enhancement of fracture healing in the rat, modulated by compounds that stimulate inducible nitric oxide synthase". The authors reported that a nutraceutical called COMB-4 consisting of L-citrulline, *Paullinia cupana*, ginger and muira puama appears to be effective in increasing the maximum strength and producing higher stiffness than the control vehicle treatment. However, other parameters such as callus volume, mineral content and bone density do not seem to show a difference between the group treated with COMB-4 versus the control group treated with vehicle.

Further, a variety of composition of nanospheres and numerous methods in the making of nanospheres, in particular fibrinogen-coated albumin spheres are known. Some examples are: (1) Therapy to reduce extravasation damage, U.S. Pat. No. 9,504,641, (2) Submicron particles to decrease transfusion, U.S. Pat. No. 9,351,925, (3) Biologic devices for hemostasis, U.S. Pat. No. 9,114,127.

However, these known nanospheres products and/or methods are concerned about hemostasis via the formation of co-aggregates with activated platelets at a wound site on the endothelium of the blood vessel. None of the published data concern the application of nanospheres for promotion of healing of bones, or the acceleration of healing of fracture bones or crushed bones.

It is therefore, not obvious that nanospheres can promote the healing of hard tissues like fractured bones and in particular, promote the reunion of non-union bone fragments.

While the above-described devices fulfill their respective, particular objectives and requirements, the aforementioned devices or systems do not describe nanospheres for healing bone fractures that allows promoting healing of fractured bones, in a surgical setting and non-surgical setting. The present technology additionally overcomes one or more of the disadvantages associated with these known products, systems and/or methods.

A need exists for new and novel nanospheres for healing bone fractures that can be used for promoting healing of fractured bones, in a surgical setting and non-surgical setting. In this regard, the present technology substantially fulfills this need. In this respect, the nanospheres for healing bone fractures according to the present technology substantially departs from the conventional concepts and designs of the prior art, and in doing so provides an apparatus primarily developed for the purpose of promoting healing of fractured bones, in a surgical setting and non-surgical setting.

SUMMARY

In view of the foregoing disadvantages inherent in the known types of known nanosphere products and/or methods now present in the prior art, the present technology provides novel nanospheres for healing bone fractures, and overcomes one or more of the mentioned disadvantages and drawbacks of the prior art. As such, the general purpose of the present technology, which will be described subsequently in greater detail, is to provide a new and novel nanospheres for healing bone fractures and method which has all the advantages of the prior art mentioned heretofore and many novel features that result in nanospheres for healing bone fractures which is not anticipated, rendered obvious, suggested, or even implied by the prior art, either alone or in any combination thereof.

According to one aspect, the present technology can include a method of stimulating bone healing in a subject in need thereof, comprising administering a therapeutically effective amount of an albumin nanoparticle suspension containing submicron albumin spheres to the subject. The albumin spheres can be configured to augment a function or effectiveness of stem cells or precursor cells in vivo.

According to another aspect, the present technology can include a composition for stimulating bone healing in a subject in need thereof, the composition can comprise a therapeutically effective amount of an albumin nanoparticle suspension containing submicron albumin spheres. The albumin spheres can be configured to augment a function or effectiveness of stem cells or precursor cells in vivo.

According to still another aspect, the present technology can include a method of using a suspension of fibrinogen-coated albumin nanospheres for intravenous administration to treat a subject to stimulate bone healing. The method can include the steps of administering intravenously a predetermined amount of an albumin nanoparticle suspension to a subject with a bone fracture. The albumin nanoparticle suspension can consist of fibrinogen-coated albumin nanospheres, sorbitol and caprylate. Stimulating in vivo bone healing in the subject by increasing a concentration of hematopoietic stem cells or precursor cells by the fibrinogen-coated albumin nanospheres administered to the subject.

Some or all embodiments of the present technology can further include the step of preparing the albumin nanoparticle suspension containing submicron albumin spheres. The albumin spheres being configured to increase a concentration of hematopoietic stem cells or precursor cells in vivo to stimulate bone healing in the subject.

In some or all embodiments, the nanospheres can be manufactured by desolvation of human serum albumin molecules from their soluble state by addition of an ethanol solution, and then cross-linking and stabilizing with glutaraldehyde to create an albumin nanoparticle solution.

Some or all embodiments of the present technology can further include the step of dissolving a solution of fibrinogen in a sodium tetradecyl sulfate (STS) solution to create fibrinogen solution, and adding the fibrinogen solution to the albumin nanoparticle solution.

Some or all embodiments of the present technology can further include the step of removing any excess ethanol, glutaraldehyde and STS molecules by dialysis.

Some or all embodiments of the present technology can further include the step of adding sorbitol and sodium caprylate to render the suspension of fibrinogen-coated albumin nanospheres iso-osmotic.

In some or all embodiments, the suspension can be administered to the subject at a dose of 16 mg spheres per kilogram weight of the subject, and can be administered within two weeks of bone trauma.

In some or all embodiments, a dosing regimen can include administration on day zero of the bone trauma, day 3 after the bone trauma, day 6 after the bone trauma, day 9 after the bone trauma and any variation thereof within the two weeks after the bone trauma.

In some or all embodiments, the precursor cells can be any one or combination of osteoblasts, endothelial progenitor cells, and stems cells in a vicinity of the bone trauma.

In some or all embodiments, the precursor cells have increased mobilization to the vicinity of the bone trauma by the stimulated production or maturation of stem cells by the administration of the suspension.

In some or all embodiments, the stimulation of bone healing can be further accomplished by an increased concentration of cytokines in serum in the subject brought on by the administration of the suspension.

In some or all embodiments, the subject can be human.

In some or all embodiments, the subject can have a bone fracture.

In some or all embodiments, the therapeutically effective amount can be 16 mg/kg administered to the subject intravenously.

In some or all embodiments, the therapeutically effective amount can be 24 mg/kg administered to the subject intravenously.

In some or all embodiments, the albumin nanoparticle suspension is administered to the subject utilizing a dosage regimen including administration at day zero, three, six and nine in relation to a bone fracture of the subject.

Some or all embodiments of the present technology can include the step of stimulating a conversion of the stem cells or precursor cells to mature cells.

In some or all embodiments, the albumin spheres of the albumin nanoparticle suspension can be bound with fibrinogen molecules to produce fibrinogen albumin spheres.

In some or all embodiments, the albumin nanoparticle suspension can include a sorbitol solution configured to maintain osmolarity compatible with blood of the subject.

In some or all embodiments, the sorbitol solution can be added to achieve a 5% sorbitol in the suspension.

In some or all embodiments, the albumin nanoparticle suspension can include a sodium caprylate solution.

In some or all embodiments, the albumin nanoparticle suspension can include a sterile protease solution to dissolve the albumin spheres and to release infectious particles trapped within the albumin spheres.

There has thus been outlined, rather broadly, features of the present technology in order that the detailed description thereof that follows may be better understood and in order that the present contribution to the art may be better appreciated.

Numerous objects, features and advantages of the present technology will be readily apparent to those of ordinary skill in the art upon a reading of the following detailed description of the present technology, but nonetheless illustrative, embodiments of the present technology when taken in conjunction with the accompanying drawings.

As such, those skilled in the art will appreciate that the conception, upon which this disclosure is based, may readily be utilized as a basis for the designing of other structures, methods and systems for carrying out the several purposes of the present technology. It is, therefore, that the claims be regarded as including such equivalent constructions insofar as they do not depart from the spirit and scope of the present technology.

It is therefore an object of the present technology to provide a new and novel nanospheres for healing bone fractures that has all of the advantages of the prior art known nanosphere products and/or methods and none of the disadvantages.

It is another object of the present technology to provide new and novel nanospheres for healing bone fractures that may be easily and efficiently manufactured and marketed.

An even further object of the present technology is to provide a new and novel nanospheres for healing bone fractures that has a low cost of manufacture with regard to both materials and labor, and which accordingly is then susceptible of low prices of sale to the consuming public, thereby making such nanospheres for healing bone fractures economically available to the buying public.

Still another object of the present technology is to provide a new nanospheres for healing bone fractures that provides in the apparatuses and methods of the prior art some of the advantages thereof, while simultaneously overcoming some of the disadvantages normally associated therewith.

These together with other objects of the present technology, along with the various features of novelty that characterize the present technology, are pointed out with particularity in the claims annexed to and forming a part of this disclosure. For a better understanding of the present technology, its operating advantages and the specific objects attained by its uses, reference should be made to the accompanying drawings and descriptive matter in which there are illustrated embodiments of the present technology. Whilst multiple objects of the present technology have been identified herein, it will be understood that the claimed present technology is not limited to meeting most or all of the objects identified and that some embodiments of the present technology may meet only one such object or none at all.

BRIEF DESCRIPTION OF THE DRAWINGS

The present technology will be better understood and objects other than those set forth above will become apparent when consideration is given to the following detailed description thereof. Such description makes reference to the annexed drawings wherein:

FIG. 3a is a representative immunostaining of irradiated a) control group, with anti-CD34 antibody in illustrated in Red and DAPI illustrated in Blue.

FIG. 3b is a representative immunostaining of irradiated b) FPS treated group, with anti-CD34 antibody in illustrated in Red and DAPI illustrated in Blue.

FIG. 4 is a graphical view of Red fluorescence intensity for the control and FPS treated group of FIG. 3.

DETAILED DESCRIPTION OF THE EMBODIMENTS

Figure 1:
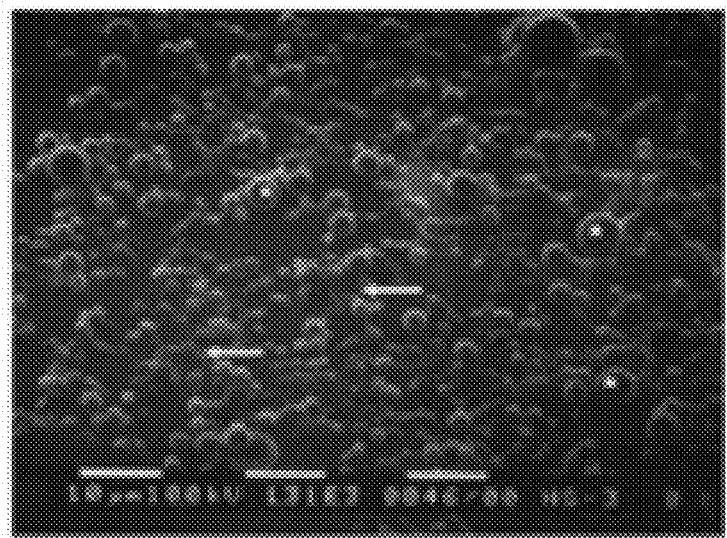
FIG. 1 is a scanning microscopy image of co-aggregates of Fibrinogen-coated albumin spheres identified with stars and human platelets identified with arrows.

In the following description, for purposes of explanation and not limitation, specific details are set forth, such as particular embodiments, procedures, techniques, etc. in order to provide a thorough understanding of the present technology. However, it will be apparent to one skilled in the art that the present technology may be practiced in other embodiments that depart from these specific details.

All scientific and technical terms used in this description have meanings commonly used in the art unless otherwise specified. The definitions provided herein are to facilitate understanding of certain terms used frequently herein and are not meant to limit the scope of the present application.

In the context of the present description, the term "A" or "an" can mean herein one or more than one; at least one. Where the plural form can be used herein, it generally includes the singular.

"Comprising" can mean, without other limitation, including the referent, necessarily, without any qualification or exclusion on what else may be included. For example, "a composition comprising x and y" encompasses any composition that contains x and y, no matter what other components may be present in the composition. Likewise, "a method comprising the step of x" encompasses any method in which x is carried out, whether x is the only step in the method or it is only one of the steps, no matter how many other steps there may be and no matter how simple or complex x is in comparison to them. "Comprised of and similar phrases using words of the root "comprise" are used herein as synonyms of "comprising" and have the same meaning.

"Comprised of" can be a synonym of "comprising" (see above).

Use of the term "includes" is not intended to be limiting.

As used herein, the term "bone loss" can refer to any situation in which skeletal mass, substance or matrix or any component of the skeleton, such as calcium and phosphate, is decreased or a bone or tooth is lost, damaged, or weakened such as in terms of its ability to resist being broken. The term "bone loss" can also encompass any situation characterized by bone deterioration, bone degradation, bone degeneration, loss of bone mass, loss of bone density, and any combinations of these conditions. The term can also be used interchangeably with "bone resorption".

As used herein, the terms "bone healing", "bone regeneration", and "remodeling" can be used interchangeably and refer to a cellular process that occurs at the cellular level. When the process becomes unbalanced, bone mass decreases and bones may become brittle. Reference to promoting bone healing or enhancing bone regeneration by the present application can imply a rebalancing of bone remodeling in such a situation. Enhancing bone repair or regeneration can refer to increasing bone repair or regeneration beyond what would normally occur in the absence of treatment using the present compositions and methods. Enhancing bone repair can include increasing the rate of bone repair and the amount of bone repair that occurs over a given time. For example, enhancing bone repair can include increasing the rate or amount of bone repair by a percentage compared with the amount or rate of bone repair or regeneration that would occur in an untreated subject.

As used herein, the terms "prevent" or "preventing" when used in the context of bone loss or bone resorption can refer to the inhibition of removal of existing bone either from the mineral phase and/or the organic matrix phase through one or variety of cellular and molecular mechanisms including, for example, direct or indirect alteration of osteoclast formation or activity. Inhibition can include complete inhibition (e.g., 100%) or substantially complete inhibition (e.g., greater than about 50%, about 60%, about 70%, about 80%, about 90%, about 95%, or about 99%).

As used herein, the terms "stimulate" or "stimulating" when used in the context of bone healing can refer to promoting bone formation (e.g., by osteoblast proliferation). The term "promoting" in respect to bone regeneration can refer to the process of increasing the amount of bone tissue, bone cells, bone cell differentiation, bone matrix, etc., in a manner that allows bone regeneration. Thus, in some instances, promoting can refer to at least about a percentage increase in bone regeneration or at least about a percentage arrest or more in bone resorption. Those of skill in the art will understand that various methodologies and assays can be used to assess the promotion of bone regeneration or healing.

As used herein, the term "subject" can refer to any warm-blooded organism including, but not limited to, human beings, rats, mice, dogs, goats, sheep, horses, monkeys, apes, pigs, rabbits, cattle, etc. When the term is used in the context of a subject needing or requiring compositions of the present application, the term may be referred to as "a subject in need thereof" and include subjects that have been clinically diagnosed (e.g., by a medical professional, e.g., a physician) as being in need of compositions of the present application, subjects that are suspected of being in need of compositions of the present application, subjects at risk for a disease or condition and who may benefit from compositions of the present application, and subjects that are already suffering from a disease or condition and who may benefit from compositions of the present application.

As used herein, the term "administered" or "administering" can refer to a route that provides for delivery of a composition or suspension of the present application to a desired compartment, system, or location. For example, administering the suspension is one through which a composition of the present application can be administered to provide at a desired site of action (e.g., a site of bone damage) an amount of the composition sufficient to effectuate a beneficial or desired clinical result (e.g., preventing bone loss and/or stimulating bone healing).

As used herein, the term "therapeutically effective amount" can refer to the amount of a composition of the present application determined to produce a therapeutic response in a subject. For example, compositions of the present application may prevent bone loss and/or stimulate bone healing in a subject in need thereof. Such therapeutically effective amounts are readily ascertained by one of ordinary skill in the art. Thus, to "treat" means to deliver such an amount.

As used herein, the terms "treat," "treating," or "treatment" are used broadly in relation to the present application and each such term can encompass, among others, ameliorating, inhibiting, or curing a bone deficiency, bone dysfunction, bone disease, or other deleterious process, including those that interfere with and/or result from a therapy. Non-limiting examples of such deficiencies, dysfunction, and disease can include bone fractures and breaks, bone defects caused by trauma or congenital conditions, osteoporosis and other osteopathy-related conditions (e.g., inflammation-induced bone loss associated with aging and rheumatoid arthritis), osteogenesis imperfect and osteomalacia, spinal fusion, and craniofacial re-construction of the mandible, maxilla, and cranial bones.

As used herein, the term "pharmaceutical composition" can refer to a preparation of one or more of the active ingredients or agents described herein (e.g., albumin nanoparticle suspension) with other components, such as physiologically suitable carriers and excipients. The purpose of a pharmaceutical composition is to facilitate administration of one or a combination of active ingredients or agents to a subject in need thereof.

Stem cells are known to be the precursors of new cells formation or tissue regeneration. The field of studying stem cells in order to encourage their conversion into mature cells that can perform specific functions in the body is called regenerative biology or regenerative medicine. Some tissues and organs are more capable of regeneration after injury, e.g. the liver. It has been known now that the new liver cells that are formed in vivo after a liver injury are not necessarily derived from the division of already-formed mature liver cells that were there in the liver before the injury, but that stem cells from their sources in the body, having migrated there from the rest of the body, become "informed" of their location and then those stem cells become liver cells. Other cells or tissues are more difficult to regenerate, e.g. nerve cells. There is a dire need for methods to encourage stem cells production in vivo which can regenerate at specific sites into new and functional cells, e.g. functional nerve cells in patients with major spinal injury. Alternatively, even if there is no net gain in the production of stem cells, but they are mobilized from the site of production to the site where they are needed or do maximum benefit, the patient will benefit.

Stem cells are called "stem cells" because they are like the stem of a tree (with one main stem or trunk) but from it there can be derived many branches (different types of functional or mature cells, depending on the kind of stimuli that the stem cells get, informing them by biochemical signals what kind of more-specialized cells to become.) Sometimes stem cells are called bone marrow cells, immature cells, or precursor cells. Depending on how "primitive" they are, they can be toti-potential, which means that they can become any kind of mature cells, depending on the kind of signal they obtain from their environment, such as those stem cells in an embryo which will eventually develop into all the organs and tissues that a new-born baby will have. Sometimes, stem cells are called pluro-potential, if they are believed to be able to develop into a plurality of cells (and not "all kinds of cells"). A lot of research has gone into signaling stem cells in vitro so that they can grow into specific tissues which may be helpful for later transplant into patients. There is little inroad in encouraging stem cells to become useful tissues in vivo, except the few cases in the generation of blood cells as mentioned in the prior art.

In the exemplary, elderly people are at great risk for bone fracture and they are more likely to suffer complications during fracture healing. Inefficient healing process exposes the elderly to higher rates of delayed healing or nonunions. The slow recovery after geriatric fractures dramatically increases risks of degenerative decline, morbidity, and mortality with a negative socioeconomic impact. Available solutions to facilitate bone regeneration are either invasive or show adverse events in aged people. Intravenous injectable Fibrinogen-coated Albumin nanospheres (FAS) are nanometer-sized spheres with a unique multi-valent potential to accelerate chronic wound healing in multiple soft tissues. FAS have been shown to promote mobilization of progenitor cells of various lineages including Endothelial Progenitor Cells (EPCs), a cell population responsible also for bone regeneration, and to counteract inflammatory states. Studies conducted on young rats showed that FAS administered after fracture promotes the superior strength and structure of the healed bone. By taking advantage of this knowledge, the present technology proposes to investigate the efficacy of Fibrinoplate-S (FPS), a FAS formulation, as biological agent to accelerate healing of fractured bones in geriatric patients. FPS could represent a new therapeutic that can improve health and functional independence of older adults. In this Phase I project it is aimed to accomplish two objectives: 1) Demonstrate the efficacy of FPS in bone fracture healing in aged pre-clinical rat models. FPS will be administered after femur surgical fracture to assess bone healing process through quantitative computed tomography, histological analysis and biomechanical evaluation of bone strength. 2) Confirm the mobilization of stem cells induced by FPS, allowing to delve deeper into their mechanism of action. This work will be preparatory of a Phase II project where an extensive IND-enabling pre-clinical study will be performed to establish metabolism, dose, and toxicity. The final goal is to obtain FDA approval of FPS as new healing agent in age-related bone fractures. By offering an effective treatment for frail patients, the present technology is expected to improve and promote healthy aging.

Fractures in elderly people are an important public health issue, especially as incidence increases with age, and the population of elderly people is growing. Treatments to accelerate geriatric bone healing are missing, exposing the elderly to a high risk of degenerative decline. The present technology includes a new biological treatment that could be easily administered to accelerate fracture healing in older adults and promote fast recovery.

It is known that there is a current problem with bone fractures in aged people due to conditions associated with bone fragility (e.g. osteoporosis, osteopenia) and a higher rate of falls due to visual impairment, problems with balance and cognitive decline. The bone healing process in the elderly is compromised due to age-dependent changes in inflammatory regulation, cellular differentiation, and signaling cascades. Complications during the fracture healing process, including delayed union and non-union, infections, internal bleeding, or heart failure, increase the risk of death among older people for up to 10 years. In addition, disability, loss of independence, and depression severely impact the quality of life. Hip fractures, considered to be the most debilitating fragility fracture are associated with an approximately 2-fold increased risk of mortality the year following the fracture. Worldwide, 9 million fractures occur each year, with heavy economic consequences on healthcare with its associated morbidity and mortality. Improved healing of first fractures may help reduce the long-term economic and clinical burden. Today nutritional supplements are given but there is no approved pharmacological treatment to accelerate the healing process in frail aged patients.

Bones fracture represents a dramatic age-related health care problem. Every year, 3.8 million Americans aged 65 or older break a bone. Older adults are at higher risk for fractures due to physiologic changes and comorbidities associated with aging including cognitive impairment, frailty, poor vision, osteoporosis, and osteopenia. For example, there is a mortality rate of 36% during the first year after a hip fracture, with 7% of elderly patients dying within the first 90 days. Fractures can permanently impair the functional status and quality of life of elderly patients similarly to the more common chronic diseases. Half of older adults will require home health care in the 6 months following a fracture, and many will have psychological disorder and long-term functional decline. In addition, almost 25% of older adults experiencing a fracture will have a second one within 5 years. Untimely, geriatric fractures in the elderly represent a significant socioeconomic burden that costs every year $20 B in medical expenditure in the US.

The current standard of care for bone fractures presents limitations in the elderly population. Despite all the developments in surgery, postoperative care and rehabilitation, there are no effective methods that promote fast bones healing. The use of electromagnetic stimulation in the treatment of fractures does not show a significant impact on delayed non-union. For example, low-intensity pulsed ultrasonography (LIPUS) fails to accelerate return to full weight-bearing and does not prevent subsequent surgery. Bone grafts represent an invasive procedure for older and frail people and it might not heal well because of other age-related medical conditions (e.g. diabetes). Numerous clinical trials examined pharmacological approaches such as Fibroblast Growth Factor-2 (FGF-2), parathyroid bone hormone PTH and other anabolic drugs, but no one has yet received FDA approval. In fact, even if these agents showed benefits in increasing bone formation, volume and density it remains to be tested whether they can prevent or treat delayed healing and non-union fractures in controlled clinical trials. Other experimental approaches based on sclerostin inhibition and the use of nutraceutical compounds for inducible nitric oxide synthase stimulation did not show accelerated fracture healing. The only pharmacological approach currently approved to improve the bone healing process is based on bone morphogenetic proteins (BMPs) mixed with osteoconductive carriers. Unfortunately, severe adverse events including infection and urogenital events cannot be handled by frail elderly patients. Therefore effective method to accelerate fracture healing in older people remains an unmet clinical need.

Poor bone healing in elderly patients prevents fast recovery. Fast bone healing in old people is impaired by physiological age-related changes that affect the process of healing, which could last for months. Studies examining the biomechanical progression of fractures have shown that elderly rats require more time to regain full mechanical strength compared to young rats. Studies on the cellular progression of tibia fractures in juvenile, middle-aged, and elderly mice demonstrated that young mice showed earlier signs of chondrocyte maturation, vascular invasion, and bone formation at the site of the fracture than elderly mice. Delayed healing in elderly patients has been attributed to impaired angiogenesis, reduced levels of growth factors and a lower capacity for mesenchymal progenitor cell division and differentiation. Osteochondral cells and their progenitors were shown to have decreased activity and quantity within the callus. Moreover, senescence of macrophages, T cells, and mesenchymal stem cells impact the inflammatory response by increasing systemic pro-inflammatory status. This age-associated inflammation is the culprit in the decline in the number and function of the skeletal stem cells that enable bones to heal. In particular, it has been shown that IL-6 elevation decreases bone formation during the repair process. Remarkably, IL-6 deletion stimulates revascularization and new bone formation, providing evidence that therapeutic strategies to block IL-6 may be beneficial for bone healing.

Tissue engineering substitutes, including osteoinductive molecules (e.g. bone morphogenetic proteins, BMPs), osteoconductive scaffolds (e.g. calcium phosphates), and osteoprogenitor cells (e.g. mesenchymal stem cells, MSCs), have been investigated as treatments for bone defects. However, these therapies have failed to translate into clinical practice. One significant limitation of these therapies is their lack of angiogenic capacity and failure to address blood supply to the tissue-engineering construct. Angiogenic cell populations, such as EPCs, have recently demonstrated the ability to affect the repair of segmental bone defects in animal models when the cells are applied acutely to freshly created defects. Published medical literature shows the potential of EPCs as an emerging strategy for the promotion of musculoskeletal regeneration. EPCs promote bone regeneration in animal models by differentiating toward endothelial cell lineages and osteoblasts, and by stimulation of vasculogenesis, angiogenesis and osteogenesis. Moreover, EPCs influence supporting cells through the secretion of growth factors and cytokines. However, the infusion of EPCs showed limitations in older patients. The major obstacles include degradation of the functionality of autologous stem cells in older individuals and difficulties in engraftment and survival of transplanted cells. Strategies to enhance and reactivate the proliferation and function of EPCs including the administration of BMP-2, growth factors such as Fibroblast Growth Factor-2 (FGF-2), and other anabolic drugs have been proposed as alternative approaches. However, possible adverse effects of the drugs, such as headache, nausea, and asthenia, may occur, especially in the elderly.

The present technology includes a new approach to accelerate bone healing in frail patients by promoting a systematic mobilization of Endothelial Progenitor Cells and the downregulation of pro-inflammatory cytokines. FPS is an injectable, ready-to-use, suspension of Fibrinogen-coated Albumin nanospheres. FPS is configured to promote the hemostatic capacity of thrombocytopenia patients, forming co aggregates with activated platelets at wound sites on the endothelium of the blood vessel, while showing extended stability and shelf life. FPS has been demonstrated to be non-toxic in pre-clinical models, while no adverse effects have been recorded in thrombocytopenic patients treated with FPS during Phase I, II and III clinical trials. Extensive studies, including a recently concluded Phase I project, revealed the ability of FPS to accelerate wound healing and self-repair of multiple ulcerated-necrotic tissues by promoting the mobilization of EPCs, and by regulating the altered expression of pro- and anti-inflammatory cytokines in the healing bone.

Preliminary data confirmed the ability of FPS to promote faster healing of hard tissues like fractured bones in young rats. The present technology aims at i) establishing the efficacy of FPS in accelerating bone healing in aged rats and ii) validate the mechanism leading to the mobilization of progenitor cells in aged rats.

Demonstrate the Efficacy of FPS in Bone Fracture Healing in Aged Pre-Clinical Models.

Fischer-344 rats aged 15 months were subjected to surgically induced open diaphyseal femoral fracture. Saline solution (control), and FPS was intravenously (IV) administered at day 0, 3, 6 and 9 post-fracture. X-ray and animal weight was monitored weekly. Quantitative computed tomography will be used to evaluate callus development and progression of union at the fracture site. Biomechanical properties will be evaluated via torsional testing at weeks 3 and 5 post-fracture. Histological analysis of bone tissue microdamage will be performed. It is expected that FPS induces faster healing in an aged pre-clinical model.

Demonstrate Mobilization of Progenitor Cells after FPS Treatment in Aged Rats.

Blood will be drawn from the control and FPS-treated group to assess the mobilization of early (CD34+, CD133−, KDR+) and mature (CD34−, CD133−, CD31+, vWF+, VE-Cadherin+) EPCs, as well as CD105+ mesenchymal stem cells. This will allow correlating the concentration of these progenitors in the blood of FPS-treated animals with any improvements in the biomechanical properties of the healed bones. To assess a possible effect of FPS on cytokines expression after a major injury, cytokines produced by immune cells will be measured. It is expected that FPS promotes progenitor cell mobilization and induces a decrease in pro-inflammatory cytokines and an increase in anti-inflammatory cytokines.

The present technology will change the clinical management of bone fractures in elderly patients by offering a new approach to promote and accelerate bone healing. FPS of the present technology can be administered intravenously (IV) after the bone trauma in both surgical and non-surgical settings. The administration of FPS will reduce the amount of sick time thanks to faster healing, promoting healthy aging. FPS will impact healthcare by reducing the cost associated with the care of geriatric fractures.

FPS is able to support accelerated wound healing of multiple ulcerated-necrotic tissues, by promoting the mobilization of different lineages of progenitor cells, and especially of EPCs, and decreasing levels of pro-inflammatory cytokines (including IL-6) in the blood. Preliminary data indicated that FPS facilitates bone formation in young rats, supporting this pre-clinical study to demonstrate the potential of FPS to facilitate bone formation in elderly patients.

Impact and Commercial Potential

Impact on Clinical Practice

Fibrinoplate-S (FPS) will change the clinical practice in geriatric fractures management by introducing a safe and biological treatment that improves and accelerates the bone healing process. FPS can be administered intravenously after the first bone trauma treatment, both in surgical and non-surgical clinical scenarios. FPS is safe with no side effects, allowing effective treatment in frail elderly patients, who cannot tolerate invasive and toxic approaches. By reducing the healing period, FPS will reduce the morbidity, mortality, and loss of productivity associated with bone fractures in the elderly. FPS is expected to reduce medical costs associated with long rehabilitation and complications after bone fractures in older adults.

Relevance to NIH Call and Contribution to Scientific Knowledge

Geriatric fractures are age-related conditions associated with functional decline and disability. FPS could represent an innovative therapeutic agent capable to accelerate the healing of fractured bones in elderly, a top priority supported by the National Institute of Aging (NIA) as well as the National Institute of Arthritis and Musculoskeletal and Skin Diseases (NIAMS). The present technology can further shed light on the mode of action of stem cells/endothelial progenitor cells during bone healing in elderly patients.

Commercial Potential

With an increasingly aging population, the fracture healing market is expected to reach $4.8 B in 2026, growing at the Compound Annual Growth Rate (CAGR) of 5% from 2018. The need to accelerate the healing process and reduce the time-span of recovery in elderly patients will drive the demand for Fibrinoplate-S as a therapeutic agent with the potential to revolutionize the fracture healing market. Leaders in fracture repair confirmed the potential of the proposed approach and offered their enthusiastic support for the validation of the new technology.

Referring to FIG. 1, FPS of the present technology FPS includes nanometer-sized spheres (diameter: 100-200 nm) that can be synthesized entirely from sterile material under aseptic conditions in a controlled environment from clinical-grade albumin and fibrinogen. The starting material to produce FAS is albumin, representing up to 60% of blood plasma proteins, and therefore fully compatible with human blood allowing systemic delivery. Once coated with fibrinogen, the nano-spheres are 10-times smaller than natural platelets (~2 μm), and they cannot obstruct even the smallest blood vessels (capillaries' diameter: ~7 μm), as best illustrated in FIG. 1, which shows a scanning microscopy of co-aggregates of Fibrinogen-coated albumin spheres (stars) and human platelets (arrows).

The production of FPS can be extracted aseptically from clinical grades of fresh-frozen plasma derived from healthy donors and specially prepared in a buffer compatible with the blank sphere suspension with high alcohol content (above 50% v/v) in order to coat the spheres without causing precipitation of the spheres.

The present technology can be utilized as or in multivalent mode of action including the augmentation of hemostatic functions, the mobilization of progenitor cells, and the reduction of inflammation state.

Regarding the augmentation of hemostatic functions, FAS was originally developed to improve the hemostatic capacity of thrombocytopenic patients by forming co-aggregates with activated platelets to serve as platelet plugs at wound sites inside the blood vessels. FPS provides an additional mass (i.e. the albumin spheres) to augment the formation of a wound-sealing clot. The sub-micron size of the FAS concentrates it near the endothelium (due to rheological effects) allowing FAS to be passively entrapped by the activated platelets to form a therapeutic clot so that the effects are localized to the wound site and not disseminated.

Regarding the mobilization of progenitor cells, studies showed the ability of FPS to promote accelerated healing of Radiation Skin Injuries (RSI) validating the present technology as an effective Medical Counter Measure for cutaneous radiation syndrome (CRS). FPS was found able to promotes the coordinated healing of deep-tissue ulcers in the skin, fat, muscle, nerve and blood vessels (see FIG. 2), confirming its ability to promote soft tissue repair. These studies revealed that FPS has a stimulatory effect on progenitor cells towards lesion. In particular FPS induced the monilization of Hematopoietic Progenitor Cells (HPCs), responsible of white blood cells production, as well as Endothelial Progenitor Cells (EPCs), able to promote accelerated wound healing and coordinated self-repair of multiple tissues.

Figure 2:
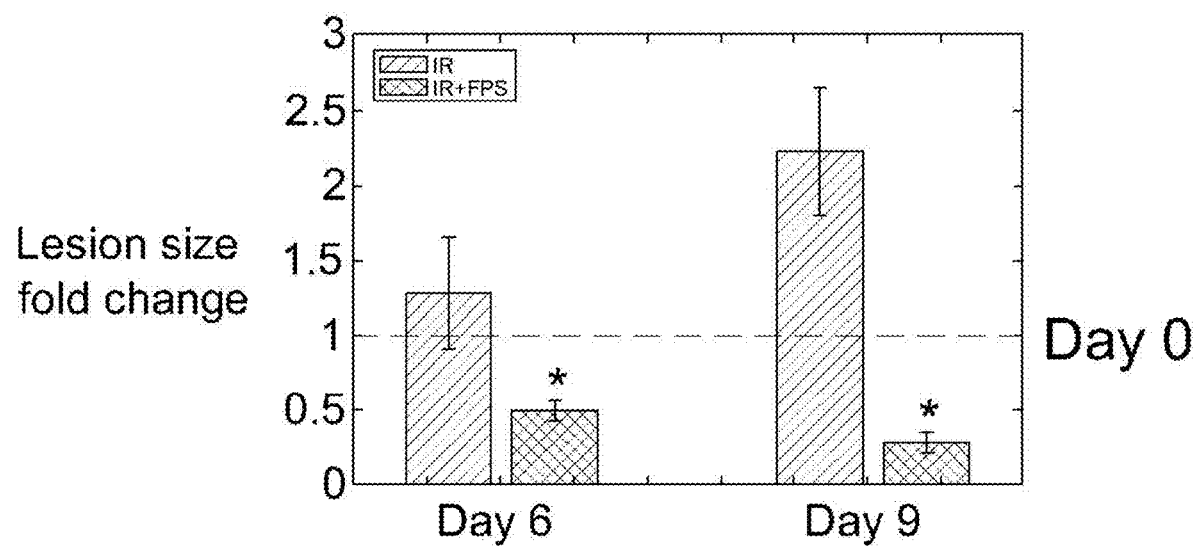
FIG. 2 is a graphical view illustrating results of the present technology promoting healing of skin injuries, where rats exposed to 25 Gy locally to the hind leg were treated with Saline (represented with angled pattern) or FPS (represented with cross pattern) when lesion appears.

FIG. 2 illustrates results of the present technology promoting healing of skin injuries, where rats exposed to 25 Gy locally to the hind leg were treated with Saline (angled pattern) or FPS (cross pattern) when lesion appears. After 9 days the average size of the skin lesion became >200% the lesion at Day 0 for the control group while it became <25% the lesion at Day 0 for the FPS treated group. Five animals/group; $*p<0.05$ vs Day 0, error bars represent SEM.

Fluorescently-labeled nanospheres were observed by two-photon microscopy to attach to the endothelial wall and then spontaneously detach after several days (see FIGS. 3a and 3b). While circulating in the vascular system, fibrinogen carried by the albumin nanospheres can interact with GlycoProtein IIb/IIIa (GPIIb/IIIa) receptors, typically present on the surface of platelets and progenitor stem cells. Once injected into the intravascular compartment the FPS spheres circulate rheologically near to the endothelium of the vascular system, distributing in arteries, veins, and capillaries, including sinusoids. The rheological properties of FPS allows direct stimulation of progenitor cells by interaction with their surface receptors. Consistent with this hypothesis, FPS administered after radiation-induced skin ulcers was able to induce mobilization of CD34+ cells to the skin lesion (see FIG. 4). The mobilization of progenitor cells by means of FPS resulted in an increased total White Blood Cell (WBC) count, offering protection against neutropenia (not shown). FIGS. 3a and 3b illustrates FPS-promoted stem cells mobilization towards radiation-induced skin lesions, where representative immunostaining of irradiated a) Control group, and b) FPS treated group (anti-CD34 antibody in RED and DAPI in BLUE). FIG. 4 illustrates RED fluorescence intensity for control and FPS treated group. ($*p<0.05$, error bars represent SEM).

Figure 5A:
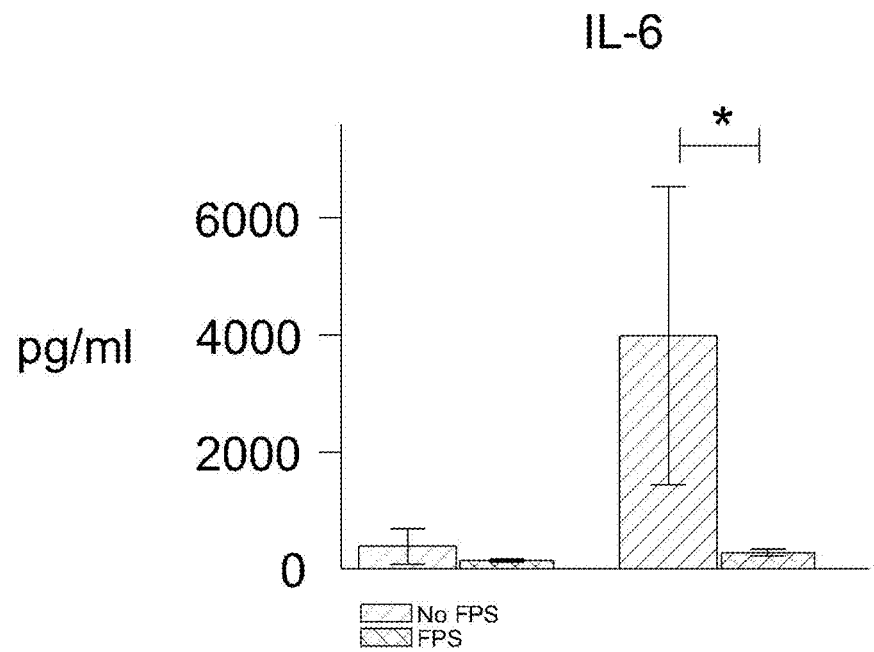
FIG. 5a is a graphical view of the effects of FPS on cytokines production with FPS treatment ameliorates the inflammatory response by inducing a reduction of pro-inflammatory IL-6 levels.
Figure 5B:
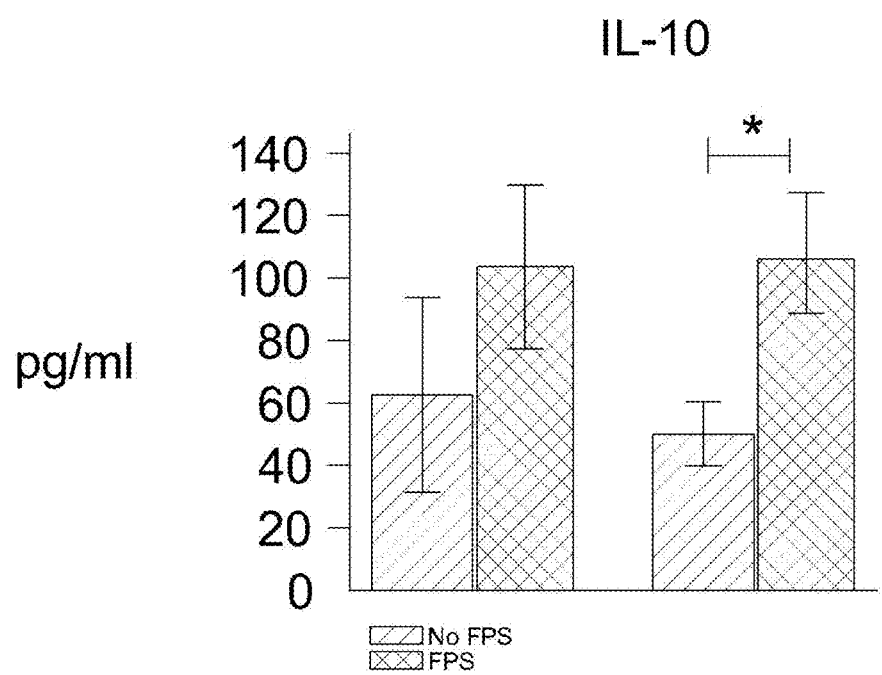
FIG. 5b is a graphical view of the effects of FPS on cytokines production with FPS treatment ameliorates the inflammatory response by inducing an increase of anti-inflammatory IL-10 levels.

Regarding the reduction of inflammation state, the administration of FPS was found able to regulate the level of several pro- and anti-inflammatory cytokines that are disregulated after radiation injuries as well as other tissue damages including broken bones. Among them, FPS was shown to ameliorate the inflammatory response by significantly reducing the amount IL-6 (see FIG. 5a). At the same time, FPS improved the inflammatory states by upregulating the anti-inflammatory IL-10 cytokine (see FIG. 5b). At this time we do not know if the effect of FPS on progenitor cells arriving at the wound site and the effect on IL6 and IL-10 are independent of each other, or related. FIGS. 5a and 5b illustrates the effects of FPS on cytokines production, where the FPS treatment ameliorates the inflammatory response by inducing: (a) reduction of pro-inflammatory IL-6; and (b) increase of anti-inflammatory IL-10 levels (b) ($*p<0.05$).

The present technology indicates that the administration of nanospheres or nanoparticles can augment the function of stem cells related to the hematopoietic system. However, the data suggest that other stem cells are also stimulated, or become increase in number in the blood, such as those that will eventually give rise to muscles, connective tissues, connective cells, and skin cells which are all involved in wound healing.

The effect of stem cell stimulation can easily be seen in patients who need certain blood cells. Patients who lack sufficient red cells, or white cells, or platelets in their blood can benefit from stem cell stimulation to result in a restoration of the normal concentration of blood cells. Numerous investigators have demonstrated that certain biological molecules, such as those produced by recombinant DNA methods (e.g. Neupogen, thrombopoietin, and erythropoietin) or naturally derived molecules can increase the production of white cells or platelets or red blood cells. However, these molecules all require the presence of a sufficient number of competent stem cells in the bone marrow and will need several days if not weeks for the stem cells to develop into mature and functional cells. The present technology can be utilized to remedy this slow-response and provides a product and a method to result in a quicker and more effective remedy to patients who can be helped by improved stem cell functions, not restricted to low blood cells counts but in all cases where stem cell functions are needed for healing.

It is now known that stem cells can be isolated from a number of tissues, not just the bone marrow, but including fat, various other organs and from the endothelium. For example, the stem cells that form bone material during the healing of bone fractures can come, at least some of them, from the endothelium. According to Aaron Nauth and Emil H Schemitsch, "Stem Cells for the Repair and Regeneration of Bone" published in Indian J Orthop. 2012 January-February; 46(1): 19-21: "Our research group and others have recently reported on the use of a novel stem cell type for enhancing fracture healing, called endothelial progenitor cells (EPCs). EPCs represent a progenitor cell population of hematopoietic origin, with known ability to participate in angiogenesis. It has been shown that EPCs home to sites of tissue ischemia, affect functional blood flow recovery in ischemic tissues, and enter the circulating system in response to trauma."

The possibility that progenitor cells of any kind or any source, or stem cells from any number of sites can be "enhanced" or "augmented" can be good news for many patients who can benefit from the enhancement. In the normal person, there is always the "battle" between the destructive processes and the healing processes. If the healing process "wins" (through perhaps the cytokines and other factors) then after the period of sickness, the patient eventually will recover, whether the recovery is 100% back to normal or not. If however, at any time the disease process or the destructive forces "wins" the patient will "turn for the worse." At any time there may be progenitor cells in all the damaged tissues trying to catch up with the healing process but there are not enough of these "good cells" or they are not maturing fast enough. Therefore, having more of these cells produced, mobilized to the wounded site, or maturing faster and in greater numbers, can be a great medical benefit. These conditions would include: damage to any major organs or large amounts of tissues, traumatic situations like crushing of bones leading to gaps where the bones cannot join up, or misaligned and non-union of the bone pieces. Sometimes the surgeons would try to use bone implants to fill the missing volume but they do not always work. The result may be the amputation of a limb. Other conditions would include spinal cord injuries leading to nerve damage, or even Alzheimer's disease.

It can be appreciated that changes in bone formation and degradation rates are coupled with adequate cellular resources that are available in the bone. Accordingly, the regulation of bone volume can be dependent not only on the pathways that mediate terminal pathways of bone cell differentiation, but also on the availability of stem cells for allowing the differentiation to occur. The ability to regulate cell numbers in stem cell compartments and the release of stem cells for differentiation of osteoblast or osteoclast precursors motivate pathological changes in bone mass. This may include effects of aging, fracture, metastatic disease, and autoimmune diseases on the precursor cell pools available for bone formation and degradation. It can be understood that increases in osteoblast or osteoclast precursors may conversely occur during growth or repair processes. The utilization of the present technology therapy based on modifying stem cell populations may, with the administration of suspension of nanospheres, assist in the healing of bone fractures, preventing chronic bone-losing states and may also be of use in preventing or treating aplastic anemia and related conditions.

To further assist in understanding the present technology, circulating osteogenic precursor (COP) cells are a population of circulating progenitor cells with the capacity to form bone and other mesenchymal tissues. COP cells are defined as a population of fluid-phase, blood-borne cells with the capacity for osteogenesis, or differentiation into mesenchymal tissues. Other terms have been used to reference COP cells, including circulating osteoprogenitors, circulating mesenchymal stem cells (cMSCs), monocyte-derived mesenchymal precursors, and circulating skeletal stem cells, amongst others.

While certain values or numbers are provided in this disclosure, it should be understood that these are only examples and only a small number of variations available to the practice of the present technology. Anyone skilled in the art may attempt to use different values or numbers to imitate this disclosure, but they are all within the scope and spirit of the present technology.

Ossification (or osteogenesis) in bone remodeling is the process of laying down new bone material by cells called osteoblasts. It is synonymous with bone tissue formation. There is a dichotomy relationship with ossification and maintenance of the skeleton between bone forming osteoblasts and resorbing osteoclasts. Osteoblasts were identified on the external surface of bone, while osteoclasts were identified in the circulation in the 1870's, and thought to be osteoblasts that had fused with a neighboring chondrocyte.

One stem cell augmentation method disclosed here comprises the intravenous administration of protein nanoparticles after the onset of the injury such as a bone fracture, where the nanoparticles have the capacity to increase concentrations of stem cells or other progenitor cells.

All of the above effects may occur in patients who are non-thrombocytopenic (normal platelet count) as well as those that are thrombocytopenia (down to 3% of the normal platelet count) and may occur in an environment of platelet dysfunction (e.g. the endogenous platelets have been inhibited by medications such as aspirin, or by other treatments such as anti-platelet antibodies, or modified antibodies).

The evaluation-method testing this treatment-method is easy to use, and can show statistically-significant differences between the control group and any of the treatment groups in a short time. This evaluation-method allows the introduction to the clinical setting new treatment-methods which can readily be shown to be superior to the standard or conventional methods to stimulate the maturation of stem cells.

It has been discovered with the present technology that a suspension of nanospheres, in particular fibrinogen-coated albumin spheres can be manufactured from medical grade human serum albumin, and the suspension is stable for at least two years of storage in ambient temperature.

It has been further discovered with the present technology that the administration of the suspension of nanospheres into a patient with bone trauma can accelerate the healing process of the damaged bone.

It has been further discovered with the present technology that a dose of 16 mg spheres per kilogram weight of the patient is effective and the dosing can be a multi-dose regiment, administered within two weeks of the bone trauma, including administration on day 0, 3, 6, 9 and any variation thereof within the two weeks.

It has been further discovered with the present technology that a dose less than 16 mg per kilogram weight of the patient can have some positive effect on the healing or the healing rate of the injured bone.

It has been further discovered with the present technology that the administration of the suspension of nanospheres can result in the improvement of the bone healing process detected by any medical equipment to comprise of at least one of the following parameters, namely callus volume, or mineral content, or bone density.

It has been further discovered with the present technology that the administration of the suspension of nanospheres can result in improvements of the bone healing process in at least one of the following mechanical parameters, namely maximum strength and stiffness.

It has been further discovered with the present technology that the administration of the suspension of nanospheres can produce better results than conventional methods in cases of crushed bones or bone fractures that conventionally will not re-join each other.

It has been further discovered with the present technology that the improved healing process is associated with the presence of any number of precursor cells to bone formation, namely more abundant osteoblasts, endothelial progenitor cells, stems cells in the vicinity of the bone injury and recovery.

It can be appreciated that the during or after bone trauma, the increased mobilization of osteoblasts, endothelial progenitor cells, stems cells to the vicinity of the bone trauma by the stimulated production or maturation of stem cells by the administration of the present technology suspension of nanoparticles promote augmentation of stem cell function.

It has been further discovered with the present technology that the improvement in healing of the bone is associated with an increased concentration of cytokines in the serum, which are associated with an increased concentration of any number of precursor cells to bone formation in the blood of the animals treated with the nanospheres of the present technology.

Experiment One

Objective

This project's aim is to determine the efficacy of fibrinogen-coated albumin spheres as agent in healing femoral fracture in male rats.

Background

Bone healing after fracture of a long bone involves a cascade of events that aim to first stabilize the fracture site, bridge the fractured ends, and remodel to its relatively original form. The first stage is to form a hematoma-like blood clot around the fracture site as the bedding for cells and growth factors. The second stage is to form a callus that is composed of cartilage from endochondral ossification processes and trabecular bone from periosteal bony proliferation. The third stage is formation of Haversian canals (blood vessel channels) through the callus that forms a bridge connecting the fractured ends. The fourth stage is the remodeling of the fracture site to its relatively original form, along with the newly adopted biomechanical milieu. The time to stabilize the fracture ends takes about 4 weeks, and a complete restored biomechanical bone may take up to two years. It is therefore quite interesting for pharmaceutical companies specializing in bone formation and osteoporosis to search for agents, biomaterials, and combinational devices to enhance the healing and reduce the time span of the healing period.

Study Materials

Test Article

The sponsor has supplied following information regarding the test article received by PharmaLegacy Laboratories.

Test article name: FPS (Fibrinoplate-S): a suspension formulation of fibrinogen coated albumin spheres which can be called nanospheres in this present technology.

The nanospheres are produced by using the manufacturing method described in "Mass Production of Ready-to-use Suspensions of Fibrinogen-coated Albumin Spheres for the Treatment of Thrombocytopenic Patients" (U. S. Publication Number 20160354481, publication date is Dec. 8, 2016, filing date is Aug. 17, 2016).

Supplier: Richard CK Yen

Description: A slightly yellow turbid suspension

Storage conditions: Ambient temperature (room temp) if unopened. Store at refrigerated temperature after removing needed test article by aseptic technique Stability: At least 2 years in ambient temperature Lot No.: Lot 2018DEC01FPS-FFLA3

Purity: >99%

The Sponsor will provide handling and disposal instructions together with any available safety information.

Data on handling and disposal instructions together with any available safety information will be retained on file at PharmaLegacy Laboratories.

Test Article Preparation

The Sponsor will provide Material Safety Data Sheets (MSDSs) and the formulation guidance for test article.

Vehicle

Reference article name: Saline

Supplier: Anhui shuanghe Pharmaceutical co. LTD

Action: Vehicle

Physical description: Transparent liquid

Storage conditions: RT

Stability: 6 months

Lot No.: TBD

Experimental Procedures

Animals

Animal species and strain: Sprague Dawley rats (SD rats)

History of treatment: Naive

Sex, age: Male, 8 weeks and older

Breeder/supplier: Vital River Laboratory Animal Technology Co., Ltd

Test Facility: PharmaLegacy Laboratories Vivarium

Adaptation: Not less than 7 days

Room: SPF Room

Room temperature: 16-26° C.

Room relative humidity: 40-70%

Light cycle: Fluorescent light for 12-hour light (8:00-20:00) and 12-hour dark

Animal hosting: Two per cage during acclimation. One rat per cage after surgery

Food: Free access to food (irradiated, Jiangsu XieTong Organism Co. Ltd., China)

Water: Free access to water (municipal tap water filtered by Mol Ultrapure Water System)

Total of 10 male SD rats will be ordered from a qualified local vendor. These rats will be approximately 8-9 weeks old upon arrival at PharmaLegacy Laboratories.

The procedures that will be applied on animals in this protocol have been approved by PharmaLegacy Laboratories IACUC.

Receipt, Health Evaluation and Acclimatization

Upon receipt animals will be placed in assigned cages. A health inspection will be performed on each animal to include evaluation of the coat, extremities and orifices. Additionally, each animal will be examined for any abnormal signs in posture or movement. The period of acclimatization should not be less than 7 days.

Environment

The animals will be housed in the PharmaLegacy Laboratories vivarium in clear polycarbonate plastic cages (400 mm×240 mm×200 mm); 2 animals per cage. The bedding material is autoclaved corn-cob bedding (Shandong Goodway Biotechnology Co., Ltd., China) that will be changed twice a week. The room number in which the animals will be housed throughout the study period will be detailed in the study records. The room will be supplied with HEPA filtered air at the rate of 15-25 air changes per hour. The temperature will be maintained at 19-26° C. (66-79° F.) with a relative humidity of 40-70%. Temperature and humidity will be continuously monitored and recorded. Illumination will be fluorescent light for 12-hour light (08:00-20:00) and 12-hour dark.

Food and Water

Animals will have ad libitum access to rodent food (irradiated, Jiangsu XieTong Organism Co. Ltd., China). The manufacturer has supplied a certificate of analysis for each batch of diet received by PharmaLegacy Laboratories. The Certificates of analysis will be retained in the PharmaLegacy Laboratories archives.

Water from PharmaLegacy Laboratories in house production will be available to animals ad libitum throughout the study period. Water, from the municipal water supply, will be filtered and sterilized by water purification system. Water analyses are performed twice per year and included analyses of heavy metals, nitrates, dissolved minerals, total plate count and coliforms. Certificates of analysis will be retained in the PharmaLegacy Laboratories archives.

It is not anticipated that the level of known contaminants in the feed and water would interfere with the purpose or conduct of this study.

Cage and Animal Identification

A unique number will be assigned to each animal. Prior to the allocation of animals to treatment groups, cages will be labeled with cards identifying study number, species/strain, sex, cage number and animal number.

After allocation to treatment groups the cages are labeled with cards which are color coded, and identify treatment groups as well as the information outlined above. Group allocation will be documented in the randomization records.

Cages will be stratified within the racks to reduce the effect of any environmental influences on the study.

Allocation to Treatment Groups

Animals will be assigned to treatment groups by randomization in BioBook system (IDBS) based on the body weights.

Total of TEN (10) male SD rats at age of 8-weeks and older will be randomized into two (2) groups of 5 animals in each group, see Table 1. First injection will be given by intravenous injection (i.v.) within one to two hours post-surgery and then doses at days 3, 6, 9, at 16 mg sphere per kg i.e. 2 mL of suspensions per kg.

TABLE 1

| Group | N | Test articles | Dosage | Dose regimen | Treatment period |
|---|---|---|---|---|---|
| 1 | 5 | Vehicle | 2 mL/kg | Day 0, 3, 6, 9; i.v. | 6-week |
| 2 | 5 | Test article | 16 mg/kg; 2 mL/kg | Day 0, 3, 6, 9; i.v. | 6-week |

Surgery

Anesthesia

Animals will be anesthetized with isoflurane 1.5-3% inhalation with a 0.8-1.5-liter flow rate of oxygen may be applied when needed.

Surgical Procedure

The right hind limb of each animal will be shaved and cleaned with 2% iodine tincture and 75% ethanol. A medial peri-patellar incision will be made, and the patella will be dislocated laterally, exposing the femoral condyles. A pilot hole will be made in the femoral trochlear groove with a 20-gauge sterile needle (about 38 mm in length); the needle will be placed through the marrow cavity until touching the endosteal surface of the lesser trochanter. A sterile Kirshner wire (1.2 mm diameter; approximately 27 mm in length) will be introduced through the pilot hole into the intra-medullary canal. The external end of the wire will be trimmed and pushed to flush against the trochlear surface. The patella will be replaced in its groove and the knee will be flexed a couple of times to ensure smooth articulation. The surgical wound will be irrigated with sterile saline after the procedures. The fascia will be closed with absorbable sutures, while skin clips will be used to close the skin incisions. After closing the skin incision, the mid-diaphysis of the pinned femur will be fractured by means of a three-point bending device driven by a single 700 g weight dropped a vertical distance of 25 cm. A highly reproducible transverse fracture will be created with minimal comminution and minimal angulation of the intramedullary pin (Bonnarens et al, 1984).

Fractures will be confirmed by Faxitron X-ray images while the animals are still anesthetized. Pain medication, Buprenorphine HCl (0.05 mg/kg, i.m.), and antibiotics, Gentamicin (20 mg/kg, i.m.), will be given. Animals having improper pin placements, comminuted or poorly located fractures will be euthanized by $CO_2$ plus cervical dislocation or cardiac bleed prior to recovery from anesthesia.

Post-Surgery Management

All animals will be monitored until they regain consciousness. Animals will be permitted full weight bearing with unrestricted activity after recovering from anesthesia. Food and water may be placed on the cage floor after surgery to ensure that the animals have access to food and water. Skin healing status will be monitored on a daily basis in addition to general health. All animals will continue to receive pain and antibiotic medication, including but not limited to Buprenorphine HCl (0.05 mg/kg, i.m.) and Gentamicin (20 mg/kg, i.m.), if pain symptoms persist. Continuation of pain/antibiotic medication, along with clinical conditions, will be documented in the Study Records.

Any of the analgesic regimens noted above may be changed based on the recommendations from the veterinarian and based on animal need for pain control. Some additional medications may be added if needed after evaluation by the Veterinarian.

If the animals show pain beyond the drug regimen listed above, the animal care staff will contact the veterinarian and the Study Director for further recommendations. All animals will be closely monitored until they recover from anesthesia. The Sponsor Representative will be made aware of medication changes and animal condition that lead to these changes by email correspondence following the veterinary consultation.

Body Weight

Animals will be weighed upon arrival and at least once weekly for the duration of treatment for health evaluation and calculation of doses.

Radiographic Analysis

Microradiographs will be taken at day ZERO (0), and weekly thereafter until necropsy at the fracture site in each rat to provide images of the connectivity of the fracture fragments, callus formation and the progress of healing.

General Observations

Animals will be observed daily for signs of ill health and general reaction to surgery and treatment. All exceptions to normal healthy appearance and behavior will be recorded and detailed in standard PharmaLegacy Laboratories clinical observations forms.

Sample Collection and Histology

After 6-week of healing, all rats will be humanely sacrificed by $CO_2$ and cervical dislocation. The fractured femurs will be collected and fixed in 10% buffered formalin after the k-wire is removed. The fixed femurs will be decalcified by formic acid and processed to paraffin blocks. Toluidine blue stain sections will be evaluated by microscopy to assess the healing by semi-quantitative assessments (0-4 scales, with 4 being the highest/best healing) focusing on amount of neovascularization and callus, bridging of the gap, and projected stability of the healing (The projected stability of a fractured bone is evaluated by the amount, the alignment and nature of the callus around and associated with the fractured bone ends).

The histology can be seen FIG. 1, which illustrates the removal of the femoral head along the dashed/dotted line, with a femoral pin intact.

Statistics

Statistical analysis will be compared by unpaired Student t-test for significance at p<0.05.

Record to be Maintained

The following documents will be collected and retained as part of the study file:
- Animal procurement, physical examination, and other pre-study health screen records
- Test compound records
- Records of cageside and other clinical observations
- Body weight data
- Correspondence relating to the study
- Original copies of protocol, amendments (if applicable) and deviations (if applicable)
- Data submitted by the Sponsor for inclusion in PharmaLegacy's report
- Report on Certificate of Analysis on the test article provided by Sponsor inclusion in PharmaLegacy's report
- Final report Archiving Draft report will be finalized and archived if a two-month period has lapsed without feedback from the sponsor. Meanwhile, the test articles and tissue samples such as unprocessed tissues, blood and urine, etc., which have been collected during the study period according to Protocol specification will be disposed as biohazardous wastes one month after the submission of the draft report, unless is otherwise required by the sponsor in writing. The paraffin embedded tissue blocks and slides will be kept at PharmaLegacy for FIVE (5) years. Beyond the time frame, sponsor will be contacted to discuss whether prolong storage will be required and additional costs will incur.

Amendments and Deviations

Protocol amendments/deviations will be produced only after approval by the Study Director and the sponsor Study Monitor.

Protocol may be amended as needed during the study period to adjust for unforeseen situations during the conduct of the study. If an amendment is warranted, a draft document will be written to detail the portion of the protocol for replacement and execution. Each amendment will be reviewed and approved by the Study Director and the Study Monitor before implementation.

Protocol deviations may occur during the study period when the described procedure is not executed accordingly as specified in the final protocol. A separate document will be written to describe the portion of the protocol that is not being executed at the time of performing the task. The corrective actions will be documented. The Study Director will provide an assessment on the impact of the deviation to the study outcome and an explanation, if needed. The deviation report will be sent to the Study Monitor immediately thereafter.

Quality Assurance and Reporting

The data are stored in a Federal Drug Administration (FDA) Part 11 compliant electronic database that has statistical package for significance analyses. This study is not subject to quality assurance (QA) audit, while all procedures will be executed according to relevant standard operating procedures (SOPs) and/or the study protocol. A draft report will be submitted for sponsor's review before finalization.

Results of Experiment One:

PharmaLegacy Laboratories reports the following for Week 4:

The microradiographs, up to the current time point at Week 4, have shown the test article group displaying a visible better healing in than all of the animals in the control group except one animal (last image of the control group). The readouts are based on the amount of callus and the fusion of the fracture ends (becoming smudged) and the rebuilding of continuity of the bone ends.

The chief scientist in PharmaLegacy believes the healing in the test article group will improve more, than the control group, at the final time point at Week 6.

The plasma of the rats will be taken at the time of sacrifice and frozen for evaluation of the increased concentration of precursor cells to bone healing, including endothelial progenitor cells and stem cells in the fibrinogen-coated albumin spheres (FPS)-treated rats compared to the saline-treated rats.

Experiment Two:

Objective:

To investigate the effect of different dosage of FPS in a rat model of an open femoral osteotomy compared to control.

Materials and Methods:

The methods of Rajfer et al is used (Bone Joint Res vol 6, no 2, February 2017) "Enhancement of fracture healing in the rat, modulated by compounds that stimulate inducible nitric oxide synthase"

The difference between the present experiment and Rajfer et al is presented below in Table 2:

TABLE 2

| | Rajfer et al | Experiment Two |
|---|---|---|
| Rats sacrificed on day | 14, 42 | 28, 42 |
| Number of Groups | Three groups: control, tadalafil, COMB-4 | Four Groups: control (saline), Group A (8 mg FPS/kg), Group B (16 mg FPS/kg, same as Experiment One) Group C (24 mg FPS/kg) |
| Number of animals per group | About 20 | About 15 |
| End Points (Improvements compared to control) | Callus Volume, Mineral Content, Bone Density | Callus Volume, Mineral Content, Bone Density |
| Immunochemistry, Biochemical markers studied | Only inducible Nitric Oxide Synthase | Inducible Nitric Oxide Synthase, Endothelial Progenitor Cells, Stem cells |
| Studies on Plasma/Serum | Not done | Cytokines indicative of increased concentrations of stem cells or other progenitor cells in the FPS treated group compared to the control group |

Results:

The results at Week 4 confirmed the findings at Pharmalegacy Lab.

The microradiographs at Week 4, have shown the test article (FPS) group displaying a visible better healing in than all of the animals in the control group. The readouts are based on the amount of callus and the fusion of the fracture ends (becoming smudged) and the rebuilding of continuity of the bone ends.

The plasma of the rats showed evidence of an increased concentration of stem cells/progenitor cells in the FPS-treated rats compared to the saline-treated rats.

The results at week 6 shows further improvements in bone healing produced by the administration of FPS compared to control animals.

In addition, the results of Group B is statistically significant compared to Group A on both Week 4 and Week 6 (Group B is better than Group A). The results in Group C are slightly better than that found in Group B. However, the results of Group C is not statistically significant over Group B, (P>0.05).

Experiment Three

Objective:

To evaluate the efficacy of fibrinogen-coated albumin spheres as an agent in promoting healing in crushed bones.

Study Material and Procedures:

They are similar to Experiment One and performed by PharmaLegacy Lab, except that instead of a clean-cut across the femoral bone, a portion of the bone is crushed so that there is a visible gap of at least 5 mm between the solid ends of the two broken pieces.

Experimental Design (See Table 3):

TABLE 3

| GROUP | N | TEST | DOSAGE | DOSE REGIMENT | Treatment Period |
|---|---|---|---|---|---|
| X | 10 | Vehicle (normal saline) | 2 mL/kg | Day 0, 3, 6, 9, i.v. | 6 weeks |
| Y | 10 | FPS (Fibrinoplate-S) | 16 mg/kg = 2 mL/kg | Day 0, 3, 6, 9, i.v. | 6 weeks |

Results:

X-ray studies showed marked improvement among animals in Group Y compared to Group X at the end of the experiment on Week 6. Although none of the animals showed complete reunion of the fragments, radiological images showed a marked increase in callus formation and other indices indicating the bones may rejoin given more time of healing in the FPS group (but not the control group.)

Conclusion:

The administration of FPS may allow reunion of otherwise non-union bone fractures. This will greatly reduce the cost of caring for patients such as military personnel who are injured during work and who may otherwise need an amputation, which would require large expenses from the government to support them for the rest of their life.

Figure 6:
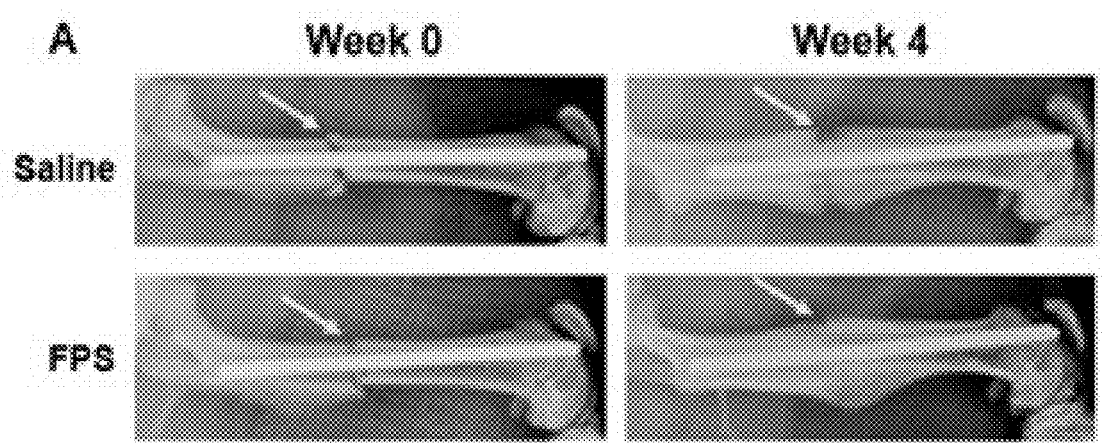
FIG. 6 is X-ray images of femoral fractures taken at Week zero (0) and Week four (4), with the arrows indicating a defect.
Figure 7:
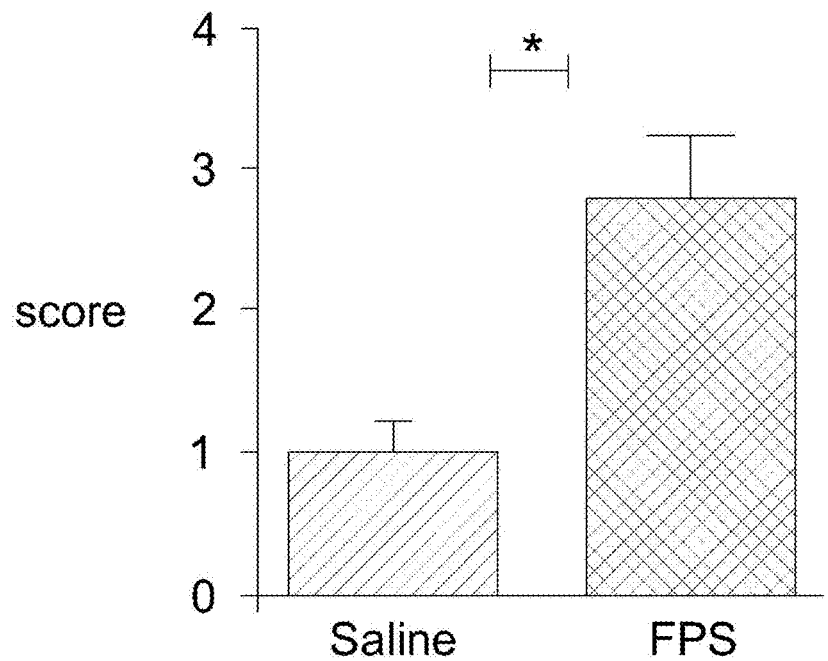
FIG. 7 is graphical view of the callus around the defect of FIG. 6.

It can be appreciated that FPS accelerates the healing process of the damaged bones. The ability of FPS to induce mobilization of Endothelial Progenitor Cells and downregulation of pro-inflammatory cytokines directed the FPS of the present technology to be utilized to heal hard tissues. The administration of FPS in femoral fractured male young Sprague Dawley rats (age: 8 weeks) was found to promote faster healing and superior structure of the healed bone compared to control saline administration. Microradiographs taken during the first four weeks after femoral fractures showed better healing in the FPS treated group based on the fusion of the fracture ends, the rebuilding, continuity of the bone ends (see FIG. 6) and the amount of callus around the fracture (see FIG. 7). No significant difference in body weights between groups was observed during the study (6 weeks), confirming the safety of FAS.

FPS can support geriatric bone healing utilizing the multivalent mode of action of FPS to promote faster progression of the healing process of soft and hard tissues. FPS will bring the advantages in the treatment of geriatric fractures compared to available solutions, as shown in Table 4 that illustrates a comparison of FPS with other approaches to treat bone fractures.

TABLE 4

| Treatment/ Producer | Healing Mechanism | Administration | Geriatric Risks |
|---|---|---|---|
| Fibrinoplate-S Fibroplate | EPCs mobilization Cytokine regulation | Systemic intravenous injection | NONE observed during FPS validation |
| Electrical stimulation Zimmer Biomet | Mechanical stress | Surgical implantation of cathodes | Increased infection rates, painful implant |
| Ultrasound Exogen Rental | Micromechanical stress | Constant use of portable device | Falls due to external device |
| Bone graft Epibone | Tissue replacement | Transplantation | Post-operative graft site infection |
| BMPs ProsSpec | Stimulation of cartilage development | Injection into fracture sites | Displacement, infection, urogenital events, ectopic bone, malignancy. |
| Anabolic Hormones Enterabio/ Novosteo | Modulation of mineral homeostasis | Ora or subcutaneous injection | Headache; nausea, vomiting, diarrhea; or joint pain. |

Some advantages of utilizing FPS to treat bone fractures can include the following.

1) Safety: The absence of side effects makes FPS a good intervention for frail geriatric patients. At present, no adverse effects (toxicity, altered blood values, thromboembolism) have been observed in animal models, nor in human subjects in Phase I, II (acute leukemia patients with thrombocytopenia).

2) Increase in White Blood Cell (WBC) count. The increase in WBCs and its subgroups (lymphocytes, Monocytes, Granulocytes) will prevent potentially deadly infections in the elderly.

3) Ease of administration: Intravenous administration of FPS will not represent an invasive approach for older adults and it will not require bulky medical instrumentations.

4) Long shelf life: Product is stable at 60° C. for at least 10 hours and has a shelf life at room temperature of 3 years. Data collected so far showed that in vivo, when the spheres are immersed in blood, the duration of activity is at least 5 days, confirming good stability of the fibrinogen-layer in biologic fluids.

FPS promotes hemostasis by forming co-aggregates with platelets. Platelet aggregation is involved in the formation of arterial thrombi in older patients, who may have predisposition to coronary obstruction or diabetes. Patients with congestive heart failure (CHF) have an increased risk of venous thromboembolism and stroke in the case of platelet abnormalities or aggregation. This aspect will be evaluated in phase II using rats with a high cholesterol level.

Rationale for Phase I Project.

FPS accelerates bone healing in young animals, expectedly due to its ability to promote EPCs to the fractured site. However, EPCs mobilization after FPS treatment might be different in aging animals compared to younger ones. The efficacy and safety of FPS in accelerating bone healing in aged rat models demonstrates it could support fracture healing in elderly patients. The project will then validate FPS' mechanism in aged animals. Findings will lead to a Phase II project where preclinical IND-enabling studies will be performed to obtain the authorization to investigate effects of FPS on geriatric fractures-healing through clinical trials. The project will cover 8 months, as shown in Table 5.

TABLE 7

| Activities | Timing (Months) | | | | | | | |
|---|---|---|---|---|---|---|---|---|
| | 1 | 2 | 3 | 4 | 5 | 6 | 7 | 8 |
| Aim 1. Demonstrate efficacy of FAS in fracture healing | X | X | X | X | X | X | X | X |
| 1.1 Fracture generation and treatment | X | X | | | | | | |
| 1.2 Evaluation bone healing process | | | X | X | X | X | | |
| 1.3 Data Analysis | | | | | | | X | M1 |
| Aim 2. Demonstrate EPCs mobilization | | | | X | X | X | X | X |
| 2.1 FACS analysis | | | | X | X | X | X | X |
| 2.2 Immunostainings | | | | | | | X | M2 |

Aim 1 and Aim 2 will include a total of 56 rats that will be divided into 4 groups as indicated in Table 5. All four groups of rats will first receive anesthesia and a femur surgically fractured. All rats will also receive subcutaneous injections of buprenorphine 0.05 mg/kg body weight for pain control. The rats will be then treated with an infusion of 16 mg spheres/kg of FPS (total dose: 2 mL per kg) or saline at day 0 (2 hours post-operation), 3, 6 and 9 following fracture. Group A (control) will be euthanized at week 3; Group B (FPS) will be euthanized at week 3; Group C (control) will be euthanized at week 5; Group D (FPS) will be euthanized at week 5. At the time of euthanasia, blood will be collected from cardiac puncture. Animal weight will be done weekly plus weekly X-rays to monitor the status of bones. After sacrifice, biomechanical properties will be evaluated in 10 rats and 4 rats will be used for histology studies (Table 6).

TABLE 6

| Aim | Group | # Rats | Injection 1 | Analysis |
|---|---|---|---|---|
| Aim 1 | # A Control 3 weeks | 10 | Saline | qCT |
| | # B Treated 3 weeks | 10 | FPS 16 mg/kg | bone mineral content bone density |
| | # C Control 5 weeks | 10 | Saline | Blood analysis |
| | # D Treated 5 weeks | 10 | FPS 16 mg/kg | Weight |
| Aim 2 | # A Control 3 weeks | 4 | Saline | Histology for Stem cells |
| | # B Treated 3 weeks | 4 | FPS 16 mg/kg | Blood analysis |
| | # C Control 5 weeks | 4 | Saline | Weight |
| | # D Treated 5 weeks | 4 | FPS 16 mg/kg | |

All Fischer-344 rats can be at the adult of age at the time of treatment. This is to reflect the therapeutic potential of FPS treatment to be applicable to the adult population. These rats are known for tendency toward osteoporosis. Seven animals at minimum for each arm can be studied in each group to reflect the need to support statistical power calculations and meaningful interpretation of the efficacy/safety for the FPS treatments. However, it should account for attrition (illness, failure of hardware/implant, unforeseen complications) so 14 rats per arm (10 for biomechanical studies and not more than 4 for histology) can be used.

Aim 1. Demonstrate the Efficacy of FPS in Bone Fracture Healing in an Aged Pre-Clinical Model.

The rationale for this is that the elderly are at higher risk for fractures due to physiological changes and comorbidities including frailty, and osteoporosis. To recapitulate this scenario Fischer-344 rat aged 15 months, which are known to have osteoporosis, will be used in this study. A 1:1 male: female ratio will be used to have a comprehensive representation of sex, which ultimately will be applicable in treating the general patient population.

Task 1.1 of fracture generation and treatment can include a surgical procedure where a total of 56 aged rats will be randomly divided into two Control and two FPS-treated groups (14 rats/group) to be sacrificed at weeks 3 and 5 post surgery. All rats will receive 3% isoflurane for anesthesia and buprenorphine 0.05 mg/kg body weight for pain control. An open diaphyseal femoral fracture will be performed with a longitudinal incision medial to the midline over the superior patella and after the medial patellar tendon border incision, the patella will be dislocated. The trochlea and the epicondyle will be opened, catclaw scissors will be placed to make a transverse osteotomy and a titanium compression IM nail (RatScrew, RISystem) achieve the fracture.

A treatment will include a saline solution (control, 2 ml/kg), and FPS (total dose: 2 ml/kg=16 mg spheres/kg) will be IV administered at day 0 (2 hours post operation), 3, 6 and 9 after fracture. This dose and the time points are based on the demonstration of accelerated bone healing in younger rats. The dose is expected to be well tolerated in the older rats, based on past repeated-dose toxicity study with no adverse effects at the highest dose tested (i.e. 24 mg/kg bw). Although FPS toxicity has been assessed in rats, bodyweight will be assessed weekly to confirm its safety in older rats.

Task 1.2 of evaluation of bone healing process can include FPS efficacy assessed by weekly microradiographs in which the readouts will be based on the callus amount, fusion of the fracture ends and rebuilding of continuity of the bone ends. The healing process will be assessed at weeks 3 and 5 post-fracture by Quantitative computed tomography (qCT) analysis (10 rats per group). The remaining 4 rats/group will be used for histological analysis of the fracture site, which will be done in Loma Linda University. The qCT will provide 3D quantitative evaluation of callus development at the fracture site and union progression. In particular, qCT will look at (a) cross-sectional transverse area, (b) callus area and (c) bone mineral density. After removal of the IM nail, a bony section 5 mm in length, which included the fracture site in the center, will be analyzed using three consecutive transverse qCT scans of 1.1 mm in thickness and 0.1×0.1 mm in pixel size. A total of 5 slices per femur will be analyzed for each rat. Five images will be obtained: two images for the bone fragment proximal to the fracture, one image for the fracture site itself and two images for the distal bone fragment. XCT Series software package (version 5.21, Stratec, Pforzheim) will be used to calculate the mineral content, mineralized callus area and bone mineral density of each image. Total mineral content and callus volume of the 5 mm segment will be calculated by combining all 3 sections values. To assess progression of remodeling, higher density callus (>500 $mg/cm^3$) will be measured and separated from total callus (>299 $mg/cm^3$). Mineral density above 850 $mg/cm^3$ is considered cortical bone density and will be eliminated from newly formed callus calculations.

Biomechanical testing can include the use of Bone Turnover Markers (BTM) to assess bone fracture repair has been shown to be unreliable94. For this reason torsional testing will be performed to assess quality of fracture repair. After CT measurement, both ends of the femurs (healed fracture and contralateral intact) will be embedded in blocks of polymethylmethacrylate. Only a 12 mm long segment of the bone (with the osteotomy in the center) will be exposed. Contralateral (intact) femur from the same rat will be treated in the same manner. Each specimen will be tested in a customized MTS machine (Mini-Bionix 858). Torsion to failure will be applied at a rate of 12 degrees/min. Four parameters will be derived from the torque-displacement curve for each specimen's load to failure test: torsional stiffness, maximum torque, angular displacement at max torque and energy required for fracture. All parameters will be normalized to the contralateral intact femur. Using the failure pattern, each specimen will be classified into one of four biomechanical stages of fracture repair. Stage I fracture is rubbery, indicating only soft callus formation. Stages II through IV exhibit higher stiffness, indicating failure of bone with progressively higher mineralized tissue. Stage I and II fractures fail through the original fracture line. Stage III failure occurred partially through the original fracture line and partially through intact bone, while Stage IV failure occurred entirely through intact bone.

Statistical analysis can include one-way analysis of variance (ANOVA) will be used to compare callus volume, bone mineral content, bone density, torsional stiffness, maximum torque at failure, angular displacement at max torque and energy required for fracture. For quantitative analysis of the histological observations values will be expressed as the mean±standard deviation of the mean (SD).

Milestone 1 can include FPS efficacy validated in an aged pre-clinical model. Expected outcomes in terms of callus development (mineral content or callus volume) can include: 1) both control and FPS groups to show at least 25% improvement at week 5 over week 3; 2) At week 3, FPS provides at least 30% faster healing than the control group; 3) At week 5, expecting more than 30% healing in FPS-treated group compared to untreated. An average weight loss in FPS-treated group more than 20% that of the normal saline-treated group over the period of the experiment without other explanations will be considered an adverse effect.

Biomechanical evaluation can include torsion-to-failure in the FAS-treated healed bone is expected to be not less than 75% of the torsion-to-fail in the contralateral intact femur from the same FAS-treated animal. The FPS group is expected to show at least 25% higher mean values of maximum torque, torsional stiffness and fracture repair stage compared to the control. Some potential pitfalls can include animals will not be restrained post-surgery. Animals that heal faster will tend to ambulate sooner with possible refracturing as the rotation movements of the bone ends under shear forces during locomotion. There is no practical way to prevent this. That is why we will study the healing bone in week 3 as well as week 5, with the expectation that healing is improved in the FPS group in week 3, even though a few FPS-treated rats may refracture before week 5.

Aim 2. Demonstrate Progenitor Cells Mobilization after FPS Treatment in Aged Rats The rationale for this is that the FPS facilitates healing of multiple tissues by inducing mobilization of EPCs, mesenchymal stem cells (MSC) and osteogenic progenitor cells. In this aim, mobilization of early (CD34+, CD133−, KDR+) and mature (CD34−, CD133−, CD31+, vWF+ and VE-Cadherin+) peripheral blood EPCs mediated by FPS will be validated. These cells are the most mature markers responsible for fracture healing.

Methodology can include blood analyses where blood will be drawn by cardiac puncture from control (28 rats) and FPS-treated rats (28 rats) sacrificed at weeks 3 and 5 (Aim 1). Blood will be analyzed by flow cytometry to quantify CD34+, CD34−, CD133−, CD31+, KDR+, vWF+ and VE-Cadherin+ progenitor cells (marker for hematopoietic progenitors), CD105+ (marker for MSC) and osteocalcin+ osteogenic progenitor as described previously to correlate their mobilization in the blood of FPS-treated animals with improvements in the biomechanical properties of the healed bones. Red blood cell, platelet and WBC counts will be also evaluated. The number of early and mature EPCs cells in peripheral blood (PB) will be calculated as the number of WBC multiplied by the percentage of gated CD34+, CD34−, CD133−, CD31+, KDR+, vWF+ and VE-Cadherin+ positive cells, and expressed as absolute cell number per 1 μL PB. Serum from all 56 rats will be analyzed to assess a possible effect of FPS on various cytokines, representing critical responses to inflammation and infection in the body. Growth factor beta (TGFβ), vascular endothelial growth factor (VEGF), interferon-γ (IFN-γ) and pro-inflammatory cytokines such as interleukin (IL)-1 and IL-6 will be measured on the same blood samples by using for example multiplex immunoassays platforms (i.e. bead-based Luminex® Bio-Rad).

Bone tissue histological analysis can include femur sections (6 μm) from random bone biopsies from around the fracture zone from 4 rats per group will be obtained and fixed. To further confirm the quality of the bone, histological analysis of the bone tissue can be done using fuchsin staining to detect microdamage. The number of early and mature EPCs, CD105+ and osteocalcin+ cells will be counted per unit area by immunostaining (counterstained with DAPI).

Statistical analysis can include one-way ANOVA to compare the different endpoints between the control- and FPS-treated groups.

Milestone 2 can include validating FPS mode of action. An expected outcomes can include: 1) a lower level of bone microdamage observed in femur sections in the FPS-treated group (75% of controls); 2) higher concentration of early and mature EPCs, CD105+ and osteocalcin+ cells is expected in the blood or at the fracture site in the FPS-treated group (120% compared to controls); and 3) statistically significant increase of SEPCs in either blood or at the bone fracture site. Some potential pitfalls can include other markers (for example. CD90 and CD73 for MSC), will be explored, if SEPC mobilization is not confirmed by the methods used in this study.

The following exemplary compositions, methods and/or processes can be utilized to prepare the albumin nanoparticle suspension of the present technology in utilization with increasing bone healing. The production of spheres in a suspension all of which are smaller than one micron in diameter can include the addition of a desovation agent in two steps.

Materials and Methods:

Human Serum Albumin (HSA) was purchased from commercial vendors including Alpha Therapeutic Corp, Los Angeles; Baxter Healthcare Corp, Glendale; Central Lab, Blood Transfusion Services, Swiss Red Cross; Immuno-US, Inc., Rochester; ZLB Bioplasma, Switzerland. Glutaraldehyde (GL) was purchased from Electron Microscopy Sciences, Fort Wash., Pa. and Sigma-Aldrich, St. Louis. Protein concentrations were measured using the BCA method from Pierce Company. To obtain the yield of the reaction, spheres were removed by high speed centrifugation to obtain the clear supernatant fraction. The difference between the total concentration of protein per ml (spheres plus supernatant) and that of the supernatant fraction was the concentration of spheres per ml. The yield of the reaction is the concentration of the spheres (in milligrams per ml) divided by the concentration of the total protein (in milligrams per ml), expressed as a percentage.

An aliquot of 25% HSA was removed from a bottle purchased from each of the above commercial vendors and diluted with distilled water to 9%. GL purchased from the above vendors was also diluted with distilled water to 0.05%. The experiment was=lied out in room temperature varying from 18° C. to 23° C. Aliquots of 100 microliters of the 9% HSA were placed in small Eppendorf tubes. At time zero (0), 100 microliters of GL (0.05%) was added to the tube and mixed thoroughly with the HSA solution.

Experiment 1A:

Addition of the desolation agent in one step. At time equal to 60 seconds after the addition of GL, various volumes of Ethanol (70% in water) were added to the mixture according to Table 7.

TABLE 7

Volume of ethanol solution added to the HAS + GL mixture in one step

| Tube number | Volume of Ethanol Solution (microliter) | Final Concentration of Ethanol | Suspension |
|---|---|---|---|
| 1 | 300 | 42.0 | Mildly turbid |
| 2 | 325 | 43.3 | Spheres formed |
| 3 | 350 | 44.5 | Aggregates Observed |
| 4 | 375 | 45.7 | Massive Aggregates |
| 5 | 400 | 46.7 | Massive Aggregates |

Experiment 1B: Addition of the desolvation agent in divided portions (two steps). At time equal to 60 seconds after the addition of GL, the first portion of Ethanol (70% in water)—a non-precipitating amount which produces no turbidity in the mixture, was added to the mixture, mixed well, and then followed by the addition of a second portion of Ethanol (70% in water) at time equal to 150 seconds after the addition of GL, as listed in Table 8.

TABLE 8 volume of ethanol used to prepare spheres in divided-portions approach

| Tube | Volume of ethanol, First portion (microliter) | Volume of ethanol, second portion (microliter) | Total vol of ethanol added (microliter) | Concentration of Ethanol in Final solution, % | Suspension | Aggregate |
|---|---|---|---|---|---|---|
| 1.0 | 50 | 0 | 250 | 38.9 | Clear, not turbid | None |
| 1.1 | 250 | 50 | 300 | 42.0 | Mildly turbid | None |
| 1.2 | 250 | 100 | 350 | 44.5 | Turbid | None |
| 13 | 250 | 150 | 400 | 46.7 | Turbid | None |
| 14 | 250 | 200 | 450 | 48.5 | Turbid | None |
| 15 | 250 | 250 | 500 | 50.0 | Turbid | None |
| 16 | 250 | 300 | 550 | 51.3 | Turbid | None |
| 17 | 250 | 350 | 600 | 52.5 | Turbid | None |

Results:

Microscopic examination of the suspensions revealed that there were no spheres in tube 10 and very few spheres in tube 1 and 11. The spheres in tube 2 was about 2 micron in diameter, while those in tube 3, 4, 5 were larger than 2 micron with large numbers of aggregates of spheres which will render the suspension unsuitable for intravenous administration to a patient because of the presence of aggregates larger than 7 micron in diameter.

In contrast, the spheres in tube 12, 13, 14, 15, 16, 17 were all smaller than one micron and had no detectable aggregates present.

The yield of the experiment (mg spheres per ml divided by mg total protein per ml) in tube 2 obtained by the one-step approach was 31%, while that of tube 12, 13, 14, 15, 16, 17 obtained by the divided-portion method were measured to be 70%, 76%, 85%, 92%, 95% and 98%, respectively.

Comments:

While the results of using HSA supplied by different vendors show variation in the size of the spheres formed as well as in the yield, the results in this experiment apply to HSA supplied by all vendors: the superiority of the divided-portion method over the one-step method is clear. In the one-step method, aggregates were formed when the final concentration of ethanol reached 44.5% (as in tube 3). In contrast, no aggregates were seen in the divided-portion approach when the final concentration of ethanol exceeds 44.5% (as in tube 12) and even at 52.5% (as in tube 17.) The yield of the spheres in any reaction appears to be directly related to the final concentration of ethanol in the tube, i.e. the higher final concentration of ethanol will produce the higher yield in spheres.

The divided-portion approach in this present technology is not obvious and is in fact contrary to the prior art teachings for the following reason. (1) The prior arts (including many of Yen's prior disclosures) have consistently taught that the addition of a desolvating agent (e.g. ethanol solution) above and beyond a critical amount to a protein solution (containing the critical amount of surfactant) will lead to irreversible formation of aggregates which cannot be separated back into individual single spheres (such as the condition in tube 3 here.) The divided-portion approach here has clearly demonstrated that the prior art teaching is no longer true given the discovery in this present technology (e.g. in tube 17 here). The volume of ethanol (70%) added to tube 17 is 600 microliters, which is 171% that of the volume (350 microliters) added to tube 3 which formed aggregates. (2) In conventional definitions: a divided portion means dividing an effective volume of the desolvating agent (e.g. 325 microliters, such as in tube 2) into smaller fractions, the sum of which will be the same as the un-divided portion (which is 325 microliter.) However, that is not the teaching here. The teaching of this present technology is (a) the first portion is not any random portion, but an amount which is subeffective. "Sub-effective" means not having a concentration that is capable of producing turbidity in the reaction mixture. In this case, when 250 microliters were added (in tube 11 to tube 17) no spheres were formed: the tubes were clear and not even mildly turbid. The sum of the first portion and the second portion will exceed significantly from the single-portion which has been shown to be effective, above which aggregates will form. However, with the divided-portion approach, even with the supra-volume or supra-mass (defined as a volume or mass that would be damaging in the one-step approach) the total added can be 171% that of an otherwise damaging volume (or mass) if added in one single step. (3) There must be a time interval between the addition of the first portion and the second portion so that the protein molecules in solution can be suitably prepared by the presence of a sub-effective concentration (i.e. a concentration that will not lead to precipitation of soluble molecules into solids) of the desolvating agent, so that when the second portion of desolvating agent is added, useful products (and not aggregates) can be formed and formed with high yield. The time interval between the first and the second portion addition in this experiment was 90 seconds but it can potentially be shorter (e.g. 15 seconds) or much longer (e.g. one hour). (4) Although the approach is called divided-portion, it is not a simple matter of dividing the desolvating agents into portions. For example, tube 5 had been added 400 micoliters of ethanol solution; so had tube 13. But the results were completely different: the contents of tube 5 could obstruct blood vessels if injected into the blood stream of a patient, leading to chest pain, a stroke or even death; whereas the contents of tube 13 have medicinal benefits with few side effects. Therefore, the mathematical similarity (the sum of ethanol being equal in those two tubes) between the two methods does not produce similar results—an obvious case of non-obviousness.

It is impressive that spheres can be formed in the absence of added detergents or surfactants to the protein solution, as taught in the prior art, yet no aggregates were formed if the desolvation agent (ethanol solution) was added in divided steps. It should be noted that in the divided-step method, the first portion of the desolvation agent must be a non-precipitation amount, i.e. to result in a concentration in the mixture unable to form protein precipitates by itself (but can produce spheres when the second portion is added.) Typically this first portion is about 85% (or a lesser quantity) of the desolvating agent that would lead to mild turbidity when added in one-step to the protein suspension, e.g. when 300 microliter of an alcohol solution will produce mild turbidity when added in a single-step to the protein solution, a good start with the divided-portion approach is to use about 250 microliters as the first-portion, to be followed by various other volumes as the second-portion to form the useful spheres.

It should be noted that in many prior art disclosures, a mixture of sizes of spheres are formed at the time of synthesis. Although efforts can be made after synthesis of the spheres to narrow the size range of the particles, such as by filtration or centrifugation to remove the unwanted fractions, significant loss of yield and significant introduction of contaminants can occur with these additional steps. The present technology results in the formation of spheres in a suspension all of which are less in one micron in diameter; the size distribution is a normal distribution with only one peak, which does not require additional steps to remove the unwanted peaks.

Experiment Two—The Optimal Time of Adding Fibrinogen to the Albumin Sphere Suspension Purpose:

To find out the optimal amount of time after the formation of spheres to allow spheres to stabilize and not redissolve upon the addition of a fibrinogen solution.

Materials and Methods:

Preliminary data had indicated the use of a sub-effective concentration (i.e. a concentration of the desolvating agent too low to prevent the resolubilization of the spheres when the alcohol concentration is reduced) of a glutaraldehyde solution (GL) added to a protein solution has the effect of producing very uniform-sized spheres. However, to stabilize the spheres against resolubilization when the desolvating agent is reduce (or removed) by dilution with fluids not containing the desolvating agent, a second portion of the linking agent (e.g. glutaraldehyde) must be added later to the sphere suspension or be present in the desolvating agent (pre-mixed into the desolvating agent.)

The method used in tube 17 of Experiment One was modified as follows: (1) 1 ml of HSA (7%) was mixed with 1 ml of GL (the sub-effective concentration being 0.125 mg/ml in water) at time zero. (2) At time 60 seconds (after addition of GL to the protein solution) the first portion of desolvating agent (ethanol 70% containing an effective concentration which is 0.5 mg of GL per ml) was added and mixed well with the protein-GL solution. The volume of the first portion was 2.5 ml, which did not produce any turbidity in the tube. (3) At time 250 second (after addition of GL to the protein solution) the second portion of desolvating agent (ethanol 70% containing also 0.5 mg of GL per ml) was added, the volume being 3.5 ml. Thereafter the turbid suspension was divided into aliquots (200 microliters each tube) and 800 microliters of water was added at various time to evaluate if the spheres had become completely stabilized against redissolving (in a solution where the effective ethanol concentration was diluted by a factor of 5 with water.)

Results:

Addition of water to a sphere suspension within 10 minutes of the formation of spheres (i.e. appearance of turbidity in the suspension) will visibly decrease the turbidity of the suspension. Assay of the concentration of spheres revealed that the yield in these tubes were only less than 5% to 10%. This confirms that the spheres formed in an adequate concentration of desolvating agents needs at least 10 minutes to stabilize. The yield of the spheres in the suspension (resistance to redissolving) increased with time between 15 minutes and reached complete stability in one hour (reaching a plateau of maximal yield of about 99%.)

The experiment was repeated with the addition of a fibrinogen solution (between 1 mg and 2 mg fibrinogen/ml) to the sphere suspension. It was found that for one volume of albumin sphere suspension, the optimal volume of fibrinogen solution to be added is between one-fifth volumes to one-third volume. Also, the optimal time to add the fibrinogen solution is about one hour after the start of the experiment (i.e. the adding of a GL solution, at 0.125 mg GL/ml to the protein solution.) The size of the spheres did not appear to change after the addition of the volume of fibrinogen solution to the volume of sphere suspension; they remain less than one micron. No aggregate were observed by microscopic examination. The sphere suspension thus prepared was stable for at least 3 days when stored in refrigerated temperature without the formation of aggregates. In contrast, the suspension formed by the single-step method (with or without the addition of fibrinogen) tended to form aggregates upon prolonged storage, unless the ethanol was removed within 6 hours of the formation of the spheres.

Administration of the suspensions of fibrinogen-coated spheres to thrombocytopenic animals (with less than 1% of the platelet concentration of their healthy counterparts) is highly efficacious. The data showed that at a dose of 4 mg spheres/kg or higher, administered intravenously, the suspensions are effective in reducing the bleeding time and the bleeding volume of these animals. It is expected that prophylactic administration of the suspension to patients who are not yet thrombocytopenic but are expected to suffer large blood loss (such as patients about to have a difficult surgical operation, or trauma patients in active bleeding who are not yet thrombocytopenic but soon will become thrombocytopenic) will also reduce the amount of blood loss in these patients during surgery or during the episode of blood-loss, and afterward.

Comments:

The yield of any industrial process must be optimized. It is found here that the best time to add the fibrinogen solution is about one hour after the addition of the GL solution to the protein solution. Adding the fibrinogen solution sooner than one hour can lead to a lower yield of the spheres due to the redissolving of the spheres which have not been completely stabilized. The volume of the fibrinogen solution should be as small compared to the volume of the sphere suspension so as not to over-dilute the concentration of the spheres: the volume of the fibrinogen solution being one third that of the volume of sphere suspension is ideal.

This requirement of about 60 minutes in between the two points in the manufacturing process (addition of fibrinogen to be delay by about one hour after appearance of turbidity) will make it extremely difficult to use a tubing system for mass production (as disclosed in the prior art by Yen.) A very long tube has to be installed to allow the portion of partially cross-linked spheres to move to the next point in the tubing system (the Y-junction) where fibrinogen molecules can then combine with the now-stabilized spheres. A very long tube is expensive and will lead to a large amount of waste (partially processed material in the "dead space") within the interior of the tubing. If the tube is long, friction with the wall of the tube will cause the material closest to the wall to move slower than the material at the center of the tube; thus the time taken to move material from one location to the next location can be very different from what is expected from the "pump rate." If the tube is particularly long, there will be areas where the tube will be curved or bent, causing very uneven flow of material around the corner—thus defeating the primary purpose of the tubing system which is to allow addition of new material at fixed time points in the manufacturing process. All these difficulties are overcome by the batch-mixing method of the present technology to be disclosed in the following experiment.

Experiment Three—Mass Production of a Ready-To-Use Formulation of Fibrinogen-Coated Albumin Spheres in Quantities of at Least 100 Liters Purpose:

To evaluate the success of the divided-portion approach to sphere formation using large quantities of materials.

Materials and Methods:

The method of Experiment Two was scaled up 10,000 times. All the containers used were sterile and had been depyrogenated by heat. The density of the various ingredient solutions was obtained by weighing a known volume of the solution. The experiment described here quotes volume measurements. However, during the actual performance of the manufacturing process, the exact volumes were dispensed or mixed by their weight, which was more accurate to measure than volume measurements. The weight of material that was to be pumped into a container was obtained by convertion from the known density of the material. Essentially: (1) 10 liters of HSA (7%) was pumped into a stainless steel drum (50 gallon capacity). (2) At time zero, 10 liters of GL (0.125 mg/ml) was added to the drum and well shaken with a specially designed platform-shaker capable of agitating quickly the contents of the 50-gallon drum. (3) At time equals to one minute, 25 liters of the first portion of desolvating agent (70% ethanol containing 0.5 mg GL/mg) was added. (4) at time equals to 2.5 minutes, 35 liters of the second portion of desolvating agent was added (same composition as the first portion). The suspension turned turbid. (5) At time equal to one hour, 20 liters of a fibrinogen solution (1 mg per ml) was added to the turbid solution. (6) The fibrinogen-coated albumin sphere suspension was then stored overnight at 5 to 9 degrees Centigrade in sterile condition.

Thereafter the suspension was dialyzed to remove as much alcohol as possible. A sterile sorbitol solution was added to achieve a 5% sorbitol in the final suspension (to maintain osmolarity compatible with blood.) A sodium caprylate solution (1%) was added to achieve a final concentration of 13.3 mg caprylate per mg protein (sphere plus soluble proteins) in the suspension. Sodium caprylate is known to provide protection of soluble protein molecules against heat denaturation. The concentration of the spheres was adjusted to 8 mg spheres/ml of the suspension.

Aliquots of 100 ml each were dispensed into each 100-ml glass vial and capped. Terminal sterilization was pertained at 65 degree Centigrade for 12 hours. Long term storage was carried out in minus 20 degrees, in 5 to 9 degrees, in 20 to 25 degrees and in 40 to 42 degrees Centigrade.

Results:

Examination under the microscope and analysis of particle size by laser technology showed that all the spheres formed by the two-step method were less than one micron in diameter and had a normal distribution with only one peak. This is in sharp contrast to the result of having several peaks of spheres (including a population larger than 7 micron in diameter) from using the method disclosed by Yen in U.S. Pat. No. 6,264,988 "Fibrinogen-coated Microspheres".

Although particular concentrations of HSA, GL and alcohol concentrations are quoted here, it is obvious that a range of concentrations of these agents (plus or minus at least 20% of the quoted values) can be used effectively. The room temperature during this experiment was 20 to 21 degrees Centigrade; but a lower or higher room temperature can be tolerated.

Sodium caprylate has been used to protect soluble proteins from denaturation by heat. It is not obvious that this compound can protect proteins in a solid form, such as a protein sphere bonded in such a way that the individual molecules at various locations in the sphere might or might not have become more susceptible to heat denaturation. Therefore, the usefulness of caprylate in this case is not obvious from the prior art.

Pyrogen content and sterility of the vials were studied after one year of storage in room temperature. The vials were shown to be free of pyrogens and infectious agents even after this duration of storage.

Administration of one ml of the suspension (i.e. containing 8 mg spheres per ml) per kilogram weight of animals that are severely thrombocytopenic showed that the suspension is effective in reducing bleeding time and the volume of blood loss, in reducing the amount of ecchymosis and in reversing the formation of petechiae in these animals. These thrombocytopenic animals typically have less than 1% of the normal concentration of endogenous platelets and have a great tendency toward spontaneous internal bleeding.

For other indications, such as treatment of burn patients, septic patients, DIC patients or patients exposed to platelet-depleting viruses, or after a lethal dose of irradiation, the effective dose of fibrinogen-coated albumin spheres may be different. Depending on the indication, the dose may be as high as 32 mg per kg weight of the patient or may be as low as 2 mg per kg weight of the patient.

There is no evidence of the formation of neoantigens on the spheres from the heat inactivation.

Careful measurement of the size of spheres in the mass-produced suspensions revealed that less than 0.1% of the spheres may be slightly larger than one micron in diameter. While these slightly larger spheres are not expected to obstruct any capillaries (which are about 6 to 7 micron in diameter) they may settle theoretically to the bottom upon prolonged storage in a container. However, it was found that if the concentration of spheres in the container is 4 mg spheres/ml or higher, the high concentration of spheres (which is about several trillions of particles per ml) which are less than one micron in diameter will keep the slightly-larger-than-one-micron spheres in suspension without the formation of any bottom layers after storage of the bottles for at least 6 months. Storage in refrigeration conditions is expected to result in substantially longer shelf-life since the refrigerator tends to vibrate during cycles of cooling.

Comments:

The success of this mass-production scheme involves more than the fact that spheres can be produced in mass quantities, or that the spheres have size distributions or other qualities similar to batches produced in more well-controlled smaller quantities. The handling of gallons of material, the need to assure absolute sterility and non-pyrogenicity of the equipment and solutions, the tendency of the material to splash and spill, all pose challenges. Therefore, it is included in this present technology a method of terminal sterilization that will ensure that even if some known or unknown infectious agents have inadvertently entered into the suspension, the infectious agents can be inactivated without harm to the spheres and the excipient components, such as by using the method to be described below.

Experiment Four—the Effect of Heat Treatment on the Inactivating of Infectious Agents Added to the Protein Solution Before the Addition of the Desolvation Agent Purpose:

To confirm that even if infectious agents were hiding in the interior of the spheres, the heat inactivation step in the terminal sterilization procedure can inactivate the infectious agents without damage to the spheres and the excipient components.

Materials and Methods:

Suspensions of fibrinogen-coated albumin spheres were prepared according to the method used in Experiment One except that infectious agents were added to the albumin solution before the addition of the desolvating agent to form spheres. The infectious agents used here include enveloped viruses (e.g. DNA viruses such as Herpes viruses, RNA viruses such as Hepatitis-D virus, Retroviruses such as Hepadnaviruses) and non-enveloped viruses (e.g. norovirus, rotavirus and human pappillomavirus—HPV). After the various sphere suspensions were prepared, they were filled into the respective glass bottled which were then capped and sealed. All the suspensions also contain a final concentration of 5% sorbitol and 13.3 mg of sodium caprylate per gram of total protein (soluble protein plus spheres) to protect the protein molecules against heat denaturation. The bottles were placed in a hot water bath and heat-treated at 65 degrees Centigrade for 12 hours. Thereafter aliquots of the sphere suspensions were aseptically removed from the glass vial; the spheres were dissolved by treatment with a sterile protease solution to release any infectious particles potentially trapped within the spheres. Titers of infectious agents were assayed and compared to positive and negative controls.

Results:

The data showed that positive controls were positive and negative controls were negative and the spheres seeded with infectious agents as described above were completely non-infectious. It showed that the heat-inactivation was effective in the inactivation of infectious agents including enveloped viruses and non-enveloped viruses. The heat treatment did not change the size of the spheres in the suspension, nor did administration of the heat-treated spheres intravenously into test animals result in any adverse clinical signs and symptoms. Administration of heat-treated suspensions to thrombocytopenic animals showed benefits similar to the administration of control, non-heat-treated suspensions which had not been seeded with infectious agents.

Comments:

Yen had disclosed inactivation of viruses and other infectious agents by extreme high pressure (see US Patent Application Publication Number 2011/0251127 A1, published on Oct. 13, 2011.) Yen disclosed that inactivation by pressure will not work in glass containers which will break under pressure. However, most commercial glass "serum" bottles can withstand heat without cracking. The data from this experiment showed that viruses that potentially can hide inside a sphere can be inactivated by the heating conditions described above even when applied to the suspension sealed inside a glass container.

It is believed that other infectious agents such as fungus, bacteria, viroids, satellites, prions, as well as derivatives of some of these agents—the spores and mutated proteins of these agents that potentially can be introduced during the manufacturing process of the ready-to-use suspension can also be inactivated by the heat treatment in this present technology without resulting in any damage to the medical benefit of the suspension and without introduction of side-effects or adverse reactions to the patient.

Sorbitol used as an excipient here is particularly useful for heat treatment. Other commonly used excipient compounds, such as glucose, maltose, or lactose, will turn dark brown (caramelization) after prolonged heat treatment, rendering the suspension dirty-looking which will be rejected by health professionals. Such degradation of the excipient component by heat, whether in chemical structure, or even just in coloration, will not be acceptable in a medical product. The suspension containing sorbitol in this present technology looks mildly yellow after the heat treatment. It is harmless to the patient and more importantly does not offer protection to the infectious agents against the heat inactivation treatment. Although sorbitol is used in the present experiment, it is believed that other excipient components which do not become discolored or become denatured by heat and which do not offer protection to infectious agents can be used.

This experiment here used spheres coated with fibrinogen. It is expected that other kinds of spheres can also be subjected to heat treatment to inactivate infectious agents successfully without damage to the medical effectiveness of the spheres, including spheres that carry other biological molecules, drugs, chemicals, DNA, RNA and radiolabeled tracing material, or even blank spheres not having any other molecules added to them during the manufacturing process.
Experiment Five—the Effect of Heat Treatment on the Inactivation of Infectious Agents Added to the Sphere Suspension after the Spheres have been Formed
Purpose:

To evaluate the success of heat treatment in the inactivation of infectious agents added to the sphere suspension after the formation of the spheres during the manufacturing process.
Materials and Methods:

The same materials and methods were used as in Experiment Four except that the respective infectious agents were added not to the protein solution but to the turbid suspensions after the spheres were formed—so that a high titer of infectious agents has the opportunity to attach to the surface of the spheres, with potential protection against heat-inactivation of the proteins and the genomic material of the infectious agents, by virtue of their close proximity to the surface of a protein sphere.
Results:

The results were similar to that of Experiment Four. It should be noted that "success" in heat inactivation includes not just the fact that the infectious agent becomes inactivated but that the spheres and the incipient components of the suspension are not adversely affected to any way by the heat treatment.
Comment:

The complete success of heat-treatment is particularly important to a ready-to-use suspension of protein spheres. If the heat-treatment is only partially successful, any infectious agent, such as a single bacterium that has survived the treatment, can have the chance to grow in this rich medium for a long time, up to a year. The turbidity of the suspension, due to the presence of the spheres will obscure the fact that some of the "particles" in such a suspension can be live bacteria. When administered to the patient, the presence of viruses, or bacteria and their toxins will cause great harm to the patient, which must not be allowed to happen and which has been shown to be preventable by the heat-treatment of this present technology.

The present technology comprises both a composition and a method. The composition is a suspension, not just the spheres in the suspension, but both the spheres and the supernatant of the suspension. Further comments and explanations are provided below.

It is a composition comprising a suspension which further comprises of (a) fibrinogen-coated albumin spheres and (b) a supernatant, where the spheres do not sediment to form a layer within six month in the supernatant, the spheres are always in contact with an aqueous phase medium since the synthesis of the spheres, said spheres have not been exposed directly to air, and said suspension is effective in the treatment of patients with bleeding problems related to platelets.

This present technology is distinguished from the prior art in at least the fact that a single population of spheres is formed which has a normal distribution ranging from about one micron to less than 0.1 micron—it has only one peak. In contrast, the prior art composition often had more than one peak at the time when the spheres were first synthesized, necessitating further steps of "purification" such as by filtration or centrifugation to remove spheres of the unwanted sizes.

The fact that spheres of the present technology do not settle to the bottom during prolonged storage indicates that the density of the spheres (weight of a sphere divided by the volume of a sphere) is very close to a value of one gram per cubic centimeter of volume, which is the density of water or of most aqueous solutions. The spheres are suspended in the supernatant by the Brownian movement of the molecules in the supernatant. The spheres do not float to the top of the container during long term storage, indicating that their density is not less than 1.00. It is expected that the density of the spheres within the population is 1.00 to 1.10 and the density of the supernatant fraction is also between 1.00 and 1.10 gram per cubic centimeter.

Whether any of the spheres have formed a sediment can be evaluated by visual inspection of the bottom of the glass container after a period of storage; or by measurement of the turbidity (or concentration of spheres) of the top fraction of the stored suspension, said top fraction will have decreased turbidity and concentration of spheres compared to the bottom fraction of the stored suspension.

Although the spheres are always suspended in an aqueous suspension since their synthesis, the aqueous medium in which they are synthesized contains a high concentration of alcohol which may not be suitable for use in some patients. The synthesis medium is also not adjusted for compatibility in osmolarity with blood. Excessive amounts of alcohol need to be removed, after which the appropriate excipient components need to be added back to the suspension to render the suspension compatible with heat treatment and intravenous administration. The "supernatant" in this present technology refers not to the medium in which the spheres are synthesized, but to the aqueous medium in the final suspension to be filled into a glass container to undergo terminal sterilization; and to the aqueous medium in which the spheres are suspended, which has undergone the terminal sterilization without damage to either the spheres or the supernatant (the heat-treated spheres and the heat-treated supernatant are collectively to be called the final product.)

It is also a composition comprising a suspension of fibrinogen-coated albumin spheres and a supernatant where the spheres at the time of synthesis are all less than one micron in diameter, said population of spheres do not sediment to form a layer within twelve months in said supernatant, said spheres are always in contact with an aqueous phase medium and have not been exposed directly to air, and said suspension is effective in the treatment of patients related to platelets.

It is also a composition where said aqueous phase medium comprises an excipient component which renders the suspension compatible with blood in osmolarity and which is not degraded by heat treatment. This present technology involves not just the spheres, but also the components in the supernatant, i.e. that of the excipient component. Both spheres and the supernatant are important to the success of the present technology because the product comprises of both the spheres and the excipient molecules in the suspension, both of which have to undergo a heat treatment for terminal sterilization.

This is a composition where said suspension including the excipient components is further subject to heat treatment under a condition where infectious agents are inactivated but where the spheres and the excipient components in the suspension are not damaged and will not cause antibody formation in a human body.

This is a composition where the heat treatment comprises heating the suspension inside a glass container to at least 60 degree centigrade, possibly to 65 degree centigrade, and for at least 10 hours, possibly 12 hours.

This present technology is also a method of mass production of suspensions of albumin spheres where the spheres have a population size-distribution at the time of synthesis of the spheres ranging from about one micron to less than 0.1 micron in diameter, with less than 0.1% of said spheres having a size greater than one micron, said spheres are always in contact with an aqueous phase medium and have not been exposed directly to air, comprising:

dissolving albumin molecules in an aqueous solution without the presence of a surfactant or detergent;

addition of a crosslinking solution which results in a sub-effective concentration for the complete crosslinking of spheres by the crosslinking agent;

(subeffective is defined here as "not capable of or not effective in" preventing the re-dissolving of the spheres when the concentration of the desolvating agent is decreased in the subsequent steps, such as from dilution by water, or from dilution by the addition of a fibrinogen-containing solution which does not have the desolvating agent in the fibrinogen-containing solution);

addition of a first portion of desolvating solution which results in a concentration of the desolvating agent insufficient to cause persistent turbidity of the mixture;

(in other words, if persistent turbidity appears after the addition of this first portion, the desolvating solution is excessive and has already produced irreversible spheres. Non-persistent turbidity is permissible because when the first portion of the desolvating agent is in the process of being added to the mixture of protein-and-crosslinking-solution, there will be localized and uneven distribution of the various components, i.e. some local areas will have high concentrations of desolvating agent temporarily reacting with the protein molecules there. Such temporary turbidity caused by inadequate mixing will immediately redissolve upon further shaking of the container to evenly distribute the components. Typically, temporary turbidity will disappear within 15 seconds of the shaking of the container to mix well the ingredient solutions); and addition of a second portion of desolvating solution after a waiting period which results in a combined concentration of the desolvating agent sufficient to cause the formation of spheres stable against redissolving and without the formation of aggregates.

This second portion will cause the formation of spheres. Although the crosslinking agent in the (b)-step is not sufficient by itself to cause complete stabilization of the spheres against redissolving, the presence of a large amount of desolvating agent in this case (the combined concentration of the first portion with the second portion) will provide some stability to the spheres thus formed, to be stable against immediately re-dissolving. It should be noted that the combined concentration of the first and second portion of desolvating agent in this present technology is far more than can be tolerated by the amount of desolvating agent used in the one-step prior art method. The vast amount of the desolvating agent in the present technology has some stabilizing effect by itself on the spheres against resolubiliztion.

Even so, to be sure that the spheres do not redissolve after one hour, additional amount of crosslinking agent can be added to both the first portion of the desolvating agent and the second portion of the desolvating agent. In the experiments described, the desolvating agent also contains 0.5 mg of glutaraldehyde per ml of the desolvating solution.

In this experiment, the recorded time of the addition of an ingredient solution is the time at the beginning of the pouring of that specific ingredient solution into the 50-gallon drum. The amount of time needed to completely pour the first portion of the desolvating agent (25 liters, as in Experiment Three) into the 50 gallon drum is typically more than 30 seconds. Therefore, the time between the beginning of the pouring of the first portion and the beginning of the pouring of the portion must be longer than 30 seconds (depending on the exact amount to be poured.) In other words, there should be a minimal time of waiting, say at least 15 seconds for the complete mixing of all the ingredient solutions that have been added so far into the 50 gallon drum. Experiment Three allowed 90 seconds between the beginning of pouring the first portion of the desolvating agent and the beginning of the pouring of the second portion—which allows adequate mixing of all the ingredients in the 50 gallon drum. Having an adequate time in between the addition of the first and the second portion of the desolvating agent is very important. This period of time will allow the first portion of the desolvating agent to adequately prepare the surface of the still dissolved albumin molecules so that they can tolerate the large amount of the second portion of desolvating agent without causing the formation of aggregates—even a smaller amount of desolvating agent would have caused massive amounts of aggregates if the desolvating solution were added in one-step, such as was used in the prior art methods.

The present technology can be utilized with a method where said mass production of suspensions of albumin spheres includes an additional step, Addition of a solution containing fibrinogen to the suspension of albumin spheres after a waiting period of about one hour after the addition of a second portion of desolvating solution, to result in suspensions of fibrinogen-coated albumin spheres.

The present technology can be utilized with a method where the yield of spheres in the suspension exceeds 80%.

The yield is defined as the concentration of spheres divided by the concentration of total proteins (total protein means spheres plus the residual soluble proteins in the supernatant) typically in one ml of suspension.

The present technology can be utilized with a method where the yield of spheres in the suspension exceeds 95%. (The yield of the prior art using the one-step method is typically only less than 30%.)

The present technology can be utilized with a method where said waiting period between the completion of the addition of first portion of desolvating solution and the beginning of addition of the second portion of desolvating solution exceeds 15 seconds.

The present technology can be utilized with a method where the concentration of spheres at the time of synthesis of the spheres exceeds one trillion spheres per ml of the suspension.

(The concentration of spheres in the final product is about 8 mg to 12 mg spheres per ml of suspension. There are very few instruments that can count the number of particles of this small size accurately. However, the weight of a sphere with a diameter of 0.4 micron can be calculated, using an estimated density of one gram per cubic centimeter. The calculation will show that the concentration of spheres with a median diameter of 0.4 micron in one ml of suspension containing 8 mg spheres/ml of suspension will exceed one trillion spheres per ml of the suspension.)

The present technology can be utilized with a method of mass production by pouring ingredient solutions into a large drum, where the volume of said suspension at the time of formation of the spheres exceeds 50 liters. (Experiment Three described adding 10 liters of GL to 10 liters of albumin solution, then 25 liters of first portion, followed by 35 liters of second portion of desolvating agent, to a total of 80 liters. The method is easily applicable to produce albumin suspensions from 50 liter to 500 liters or even larger volumes.)

The present technology can be utilized with method of mass production of a ready-to-use suspension where the desolvating agent is ethyl alcohol and where the concentration of said ethyl alcohol at the time when the spheres are synthesized is at or above 45% in the suspension.

Figure 8:
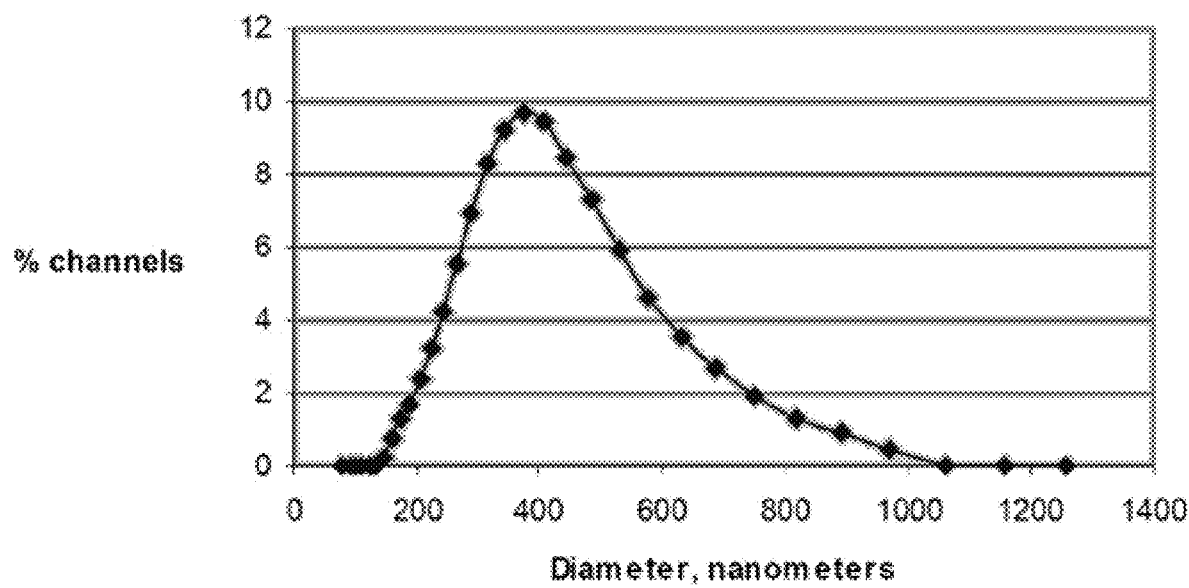
FIG. 8 is graphical view of the size distribution of the spheres in the FPS of the present technology.

The following information defines the chemical, physical and biological composition of FAS. A sample of FAS has been analyzed by Microtrac Inc., Largo, Florida FIG. 8 shows the distribution of the size (diameter) of the spheres. Table 9 is a summary of the other physical parameters of the spheres composing FAS.

TABLE 9

| Parameter Measured | Value |
| --- | --- |
| Mean Diameter of the number distribution | 263 nanometers |
| Mean Diameter of the volume distribution | 389 nanometers |
| Mean Diameter of the area distribution | 340 nanometers |
| Standard Deviation | 137 nanometers |
| Calculated Surface | 17.6 sq meter/cc |
| Molecular Weight | 1.5E+10 grams/mole |
| Inclusive Graphic Skewness | 0.243 |
| Kurtosis (Peakedness) | 1.103 |

The spheres can be manufactured by desolvation of human serum albumin molecules from their soluble state by the addition of an ethanol solution, and then are cross-linked and stabilized with glutaraldehyde. Then a solution of fibrinogen dissolved in an STS (Sodium Tetradecyl Sulfate) solution (not more than 2 mg STS/ml) can be added. Excess ethanol, glutaraldehyde and STS molecules can then removed by dialysis. Excipients (Sorbitol and caprylate) can be subsequently added to the suspension to render it iso-osmotic. Then the suspension is filled into 50 ml bottles and terminally sterilized. A list ingredients that can be involved in FAS production, the amount and purpose is shown in Table 10.

TABLE 10

| Component | Amount | Purpose |
| --- | --- | --- |
| Human Albumin spheres | Not less than 8 mg/ml | To provide a preformed mass which is capable of being entrapped passively by activated platelets (thereby forming a co-aggregate) during the formation of a hemostatic clot at a wound site. |
| Human Fibrinogen | Not more than 0.05 mg Fibrinogen per mg Albumin sphere | To provide a substrate for thrombin to react with, so that the resulting fibrin molecules associated with the spheres can form a crosslinking mass with fibrin derived from soluble fibrinogen in the plasma as well as fibrin derived from fibrinogen on the surface of activated platelets. |
| Ethanol | Not more than 6% | Ethanol (about 80%) is used to desolvate soluble albumin molecules into spheres. The ethanol is not completely removed during dialysis. Not more than 6% of ethanol is present in the final suspension product. |

TABLE 10-continued

| Component | Amount | Purpose |
| --- | --- | --- |
| Glutaraldehyde | Not more than 0.04 mg/ml | Glutaraldehyde is used to crosslink the protein spheres so that on the removal of the high concentration of ethanol during dialysis, the spheres do not re-dissolve. There is no reactive aldehyde group left in the final product; all the added glutaraldehyde molecules will have reacted with the protein molecules in the suspension. |
| Sodium Tetradecyl Sulfate (STS) | Not more than 0.02 mg/ml | A solution of STS not more than 2 mg/ml is used to dilute a stock fibrinogen solution to about 2 mg of fibrinogen/ml before the diluted fibrinogen solution is added to the sphere suspension. After dialysis to remove excess ethanol and further processing, the STS in the final product will not be more than 0.02 mg/ml. |
| Sorbitol | 50 mg/ml | An excipient added to the final suspension to render the suspension iso-osmotic with plasma. |
| Sodium Caprylate | 13.3 mg per gram of protein in the suspension | An excipient added to the final suspension to provide protection for the protein during terminal sterilization, which is done by heating the content inside. |

The spheres in FAS are inert in vitro and do not cause aggregation of blood cells (including platelets) in the absence of platelet-activating molecules. The spheres are made of cross-linked human serum albumin molecules coated with human fibrinogen (not to exceed 0.05 mg of fibrinogen per mg of albumin sphere.) The adsorbed fibrinogen molecules are stable and do not detach from the spheres. In vitro, in the fluid containing excipients, the fibrinogen is stably attached at 60° C. for at least 10 hours (during terminal pasteurization) and the shelf life of the product at room temperature is 3 years. In vivo, where the spheres are immersed in blood (with 2 mg of fibrinogen per mL blood), the duration of activity is at least 5 days and the FAS is still effective in improving bleeding time. The concentration of fibrinogen can be measured with a competitive immunoassay using known concentrations of fibrinogen solutions as standards for comparison. FAS does not contain thrombin. In vivo, the thrombin molecules that participate in a clot formation come from the patient's endogenous plasma prothrombin molecules. In vivo, the activity of thrombin on the FAS is the same as described by the classic coagulation pathway. At the wound site, platelets are activated. Prothrombin molecules are converted on the surface of activated platelets to thrombin molecules which remain attached to the platelet membrane. This membrane-associated thrombin is very active and cleaves fibrinogen from 3 sources: (a) from the soluble fibrinogen in the plasma, (b) the fibrinogen on the surface of activated platelets, and (c) the fibrinogen on the surface of FAS spheres. The resultant fibrin monomers from all 3 sources accumulate spontaneously to form a solid fibrin/platelet/sphere mass (i.e. the co-aggregate).

Prior to release and in the exemplary, the FPS can be subject to meet predetermined specifications, as shown in Table 11.

TABLE 11

| Attribute | Method Name | Method Number | Acceptance Criteria |
| --- | --- | --- | --- |
| Appearance | Visual | N/A | Turbid, slightly yellow color. |

TABLE 11-continued

| Attribute | Method Name | Method Number | Acceptance Criteria |
|---|---|---|---|
| Identity | Functional Test | Q-0019-v01r01 | Formation of sphere-augmented fibrin clot |
| pH | USP<791> | USP<791> | pH 6.2 to 7.0 |
| Osmolarity | USP<785> | USP<785> | Not less than 350 mOsm/L |
| Particle Size | Laser Diffraction Particle Size Analysis | Microtrac | Median diameter <0.5 um, and no diameters >5 um |
| Purity | Laser Diffraction Particle Size Analysis | Microtrac | >99% (Purity = % sphere diameters <1 um) |
| Potency | Functional Test | Q-0019-v01r01 | >1 activity unit |
| Sterility | USP<71> | USP<71> | No Growth |
| Endotoxin | USP<85> | USP<85> | <2.9 EU/ml |
| Quantity | USP<1057>, BCA Method | Q-0014-v01r01 | 6.5-9.5 mg/mL (Quantity = mg/mL suspension-mg/mL supernatant) |

While embodiments of the nanospheres for healing bone fractures have been described in detail, it should be apparent that modifications and variations thereto are possible, all of which fall within the true spirit and scope of the present technology. With respect to the above description then, it is to be realized that the optimum dimensional relationships for the parts of the present technology, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present technology. For example, any suitable sturdy material may be used instead of the above-described. And although promoting healing of fractured bones, in a surgical setting and non-surgical setting have been described, it should be appreciated that the nanospheres for healing bone fractures herein described is also suitable for augmenting stem cell function in vivo and/or treat radiation-induced skin ulcers.

Therefore, the foregoing is considered as illustrative only of the principles of the present technology. Further, since numerous modifications and changes will readily occur to those skilled in the art, it is not desired to limit the present technology to the exact construction and operation shown and described, and accordingly, all suitable modifications and equivalents may be resorted to, falling within the scope of the present technology.

The invention claimed is:

1. A method of maintaining bone health in a subject while the subject is uninjured, unwounded or does not have a bone fracture, the method comprising administering a first therapeutically effective amount of an albumin nanoparticle suspension containing submicron albumin spheres to the subject, the albumin spheres being configured to augment a function or effectiveness of stem cells or precursor cells in vivo to simulate bone healing in the subject by promoting a mobilization of endothelial progenitor cells and a downregulation of pro-inflammatory cytokines and to maintain bone health by adding to a mineral content of bone of the subject by work of the stem cells or the precursor cells, wherein the suspension is administered intravenously.

2. The method of claim 1, wherein the subject is human.

3. The method of claim 1, wherein the therapeutically effective amount is 16 mg/kg.

4. The method of claim 1, wherein the therapeutically effective amount is 24 mg/kg.

5. The method of claim 1, wherein the albumin nanoparticle suspension is further administered to the subject utilizing a dosage regimen including administration at day zero, three days, six days and nine days in relation to a bone fracture of the subject.

6. The method of claim 1 further comprising the step of stimulating a conversion of the stem cells or precursor cells to mature cells.

7. The method of claim 1, wherein the albumin spheres of the albumin nanoparticle suspension are bound with fibrinogen molecules to produce fibrinogen albumin spheres.

8. The method of claim 1, wherein the albumin nanoparticle suspension includes a sorbitol solution configured to maintain osmolarity compatible with blood of the subject.

9. The method of claim 8, wherein the sorbitol solution is added to achieve a 5% sorbitol in the suspension.

10. The method of claim 9, wherein the albumin nanoparticle suspension includes a sodium caprylate solution.

11. The method of claim 1, further comprising the step of administering to the subject, after the administration of the first therapeutically effective amount and in relation to a bone fracture, a dosage regimen of the albumin nanoparticle suspension continuously for three days after the bone fracture, wherein the albumin nanoparticle suspension includes a sterile protease solution to dissolve the albumin spheres and to release infectious particles trapped within the albumin spheres.

* * * * *